(12) United States Patent
Yokoyama et al.

(10) Patent No.: US 8,722,209 B2
(45) Date of Patent: *May 13, 2014

(54) COMPOUND HAVING PYRIDOINDOLE RING STRUCTURE HAVING SUBSTITUTED PYRIDYL GROUP ATTACHED THERETO, AND ORGANIC ELECTROLUMINESCENCE ELEMENT

(75) Inventors: Norimasa Yokoyama, Tsukuba (JP); Shuichi Hayashi, Tsukuba (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/419,849

(22) Filed: Mar. 14, 2012

(65) Prior Publication Data

US 2012/0298969 A1 Nov. 29, 2012

Related U.S. Application Data

(63) Continuation of application No. 12/377,908, filed as application No. PCT/JP2007/065963 on Aug. 16, 2007, now Pat. No. 8,168,308.

(30) Foreign Application Priority Data

Aug. 18, 2006 (JP) ................................ 2006-222890

(51) Int. Cl.
*H01L 51/54* (2006.01)
*C07D 471/04* (2006.01)

(52) U.S. Cl.
USPC ........... 428/690; 428/917; 313/504; 313/506; 546/84

(58) Field of Classification Search
None
See application file for complete search history.

(56) References Cited

U.S. PATENT DOCUMENTS

| | | | | |
|---|---|---|---|---|
| 8,168,308 | B2 * | 5/2012 | Yokoyama et al. | 428/690 |
| 2005/0079387 | A1 | 4/2005 | Lee et al. | |
| 2010/0123388 | A1 | 5/2010 | Yokoyama et al. | |
| 2010/0308322 | A1 * | 12/2010 | Yokoyama et al. | 257/40 |
| 2011/0073852 | A1 * | 3/2011 | Yokoyama et al. | 257/40 |
| 2011/0175079 | A1 * | 7/2011 | Yokoyama et al. | 257/40 |
| 2011/0272679 | A1 * | 11/2011 | Yokoyama et al. | 257/40 |
| 2012/0126220 | A1 * | 5/2012 | Yokoyama et al. | 257/40 |

FOREIGN PATENT DOCUMENTS

| | | | |
|---|---|---|---|
| EP | 1 571 193 A1 | | 9/2005 |
| JP | 2001 160488 | | 6/2001 |
| JP | 2004 311415 | | 11/2004 |
| JP | 2005 120085 | | 5/2005 |
| JP | 2006 32599 | | 2/2006 |
| JP | 2006 128257 | | 5/2006 |
| JP | 2006 156445 | | 6/2006 |
| JP | 2007-180147 | * | 7/2007 |
| JP | 2008-158445 | | 7/2008 |
| JP | 20080158445 | | 7/2008 |

OTHER PUBLICATIONS

Translation of JP 2007-180147 (publication date Jul. 2007).*
Machine translation for JP 2007-180147, publication date of Jul. 2007.
Machine tranlation for JP 2006-156445, which has a publication date of Jun. 2006.
Machine translation for JP 2006-128257, publication date of May 2006 (printed as parts 1 and 2).

* cited by examiner

*Primary Examiner* — Dawn L. Garrett
(74) *Attorney, Agent, or Firm* — Oblon, Spivak, McClelland, Maier & Neustadt, L.L.P.

(57) ABSTRACT

The invention relates to a compound having a pyridoindole ring structure having a substituted pyridyl group of formula (1); and to an organic electroluminescent device comprising a pair of electrodes and at least one organic layer interposed between the electrodes, wherein at least one of the organic layer(s) contains the compound:

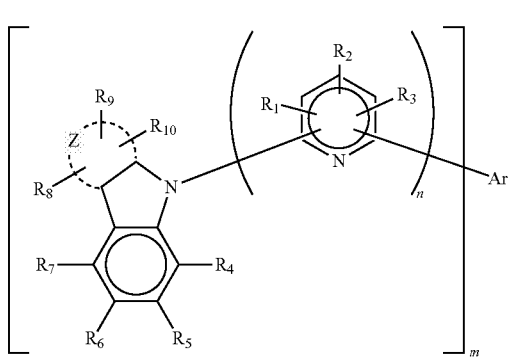

(1) wherein Ar represents a substituted or unsubstituted aromatic hydrocarbon group, a substituted or unsubstituted aromatic heterocyclic group, or a substituted or unsubstituted condensed polycyclic aromatic group; R1 to R10 may be the same or different from one another and each independently represents a hydrogen atom, a fluorine atom, a cyano group, an alkyl group, or a substituted or unsubstituted aromatic hydrocarbon group; Z represents a 6-membered aromatic heterocyclic ring containing one nitrogen atom; and m and n each independently represents an integer of 1 to 3, provided that n is 1 when m is 2 or 3.

12 Claims, 13 Drawing Sheets

COMPOUND HAVING PYRIDOINDOLE RING STRUCTURE HAVING SUBSTITUTED PYRIDYL GROUP ATTACHED THERETO, AND ORGANIC ELECTROLUMINESCENCE ELEMENT

This application is a continuation application of U.S. Ser. No. 12/377,908 filed on Feb. 18, 2009, which is a U.S. National Stage filing of PCT/JP07/65963 filed on Aug. 16, 2007.

TECHNICAL FIELD

The present invention relates to a compound suitable for an organic electroluminescence (EL) device which is a self-luminescent device suitable for various displaying devices and a device. More specifically, it relates to a compound having a pyridoindole ring structure having a substituted pyridyl group attached thereto, and to an organic EL device using the compound.

BACKGROUND ART

Since organic EL devices are self-luminescent devices, they are bright and excellent in visibility as compared with liquid-crystalline devices and capable of giving clear display, so that the organic EL devices have been actively studied.

In 1987, C. W. Tang et al. of Eastman Kodak Company put an organic EL device using organic materials into practical use by developing a device having a multilayered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m² or more at a voltage of 10 V or lower (see e.g., Patent Documents 1 and 2).
Patent Document 1: JP-A-8-48656
Patent Document 2: Japanese Patent No. 3194657

To date, many improvements have been performed for practical utilization of the organic EL devices, and high efficiency and durability have been achieved by an electroluminescent device wherein an anode, a hole-injecting layer, a hole-transporting layer, an emitting layer, an electron-transporting layer, an electron-injecting layer, and a cathode are sequentially provided on a substrate, to further segmentalize various roles (see e.g., Non-Patent Document 1).
Non-Patent Document 1: Japan Society of Applied Physics Ninth Workshop Preprint pp. 55-61 (2001)

Further, for the purpose of further improvement of luminous efficiency, utilization of triplet exciton has been attempted and utilization of a phosphorescent material has been investigated (see e.g., Non-Patent Document 2).
Non-Patent Document 2: Japan Society of Applied Physics Ninth Workshop Preprint pp. 23-31 (2001)

The emitting layer can be also prepared by doping a carrier-transporting compound, generally called a host material, with a fluorescent material or a phosphorescent material. As described in the above-mentioned Workshop Preprints, the choice of the organic materials in organic EL devices remarkably affects efficiency and durability of the devices.

In the organic EL devices, the charges injected from the both electrode are recombined in the emitting layer to attain light emission. However, since the mobility of holes is higher than the mobility of electrons, a problem of reduction in efficiency caused by a part of the holes passing through the emitting layer arises. Therefore, it is required to develop an electron-transporting material in which the mobility of electrons is high.

A representative light-emitting material, tris(8-hydroxyquinoline)aluminum (hereinafter referred to as Alq) is commonly used also as an electron-transporting material but it cannot be considered that the material has hole-blocking capability.

As a technique to prevent the passing of a part of holes through the emitting layer and to improve probability of charge recombination in the emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (Balq) (see e.g., Non-Patent Document 2), and the like.

For example, as an electron-transporting material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).
Patent Document 3: Japanese Patent No. 2734341

Since TAZ has a work function as large as 6.6 eV and thus exhibits a high hole-blocking ability, it is used as an electron-transporting hole-blocking layer to be laminated onto the cathode side of a fluorescence-emitting layer or phosphorescence-emitting layer prepared by vacuum deposition, coating or the like, and contributes to increase the efficiency of organic EL devices (see e.g., Non-Patent Document 3).
Non-Patent Document 3: Fiftieth Meeting of Japan Society of Applied Physics and Related Societies, 28p-A-6 Lecture Preprint p. 1413 (2003)

However, TAZ has a great problem of having low electron transport property, and it is necessary to prepare an organic EL device in combination with an electron-transporting material having a higher electron transport property (see e.g., Non-Patent Document 4).
Non-Patent Document 4: Japan Society of Applied Physics, Journal of Organic Molecules/Bioelectronics Section, Vol. 11, No. 1, pp. 13-19 (2000)

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in film stability or are insufficient in the function of blocking holes. In order to improve characteristic properties of the organic EL devices, it is desired to develop an organic compound which is excellent in electron-injection/transport performances and hole-blocking ability and is highly stable in a thin-film state.

DISCLOSURE OF THE INVENTION

Problems to be Solved by the Invention

Objects of the invention are to provide an organic compound which is excellent in electron-injection/transport performances, has hole-blocking ability and is highly stable in a thin-film state as a material for an organic EL device having a high efficiency and a high durability, and to provide an organic EL device having a high efficiency and a high durability using the compound. As physical properties of the organic compound suitable for the invention, there may be mentioned (1) good electron injection characteristic, (2) high electron mobility, (3) excellent hole-blocking ability, (4) good stability in a thin-film state, and (5) excellent thermal resistance. In addition, as physical properties of the device suitable for the invention, there may be mentioned (1) high luminous efficiency, (2) low emission initiation voltage, (3) low practical driving voltage, and (4) high maximum emission luminance.

Means for Solving the Problems

Thus, in order to achieve the above objects, the present inventors have designed and chemically synthesized compounds having a pyridoindole ring structure having a substituted pyridyl group attached thereto, with focusing on the fact that the nitrogen atom of the pyridine ring which exhibits affinity to an electron has an ability of coordinating to a metal and is excellent in thermal resistance. The present inventors have experimentally produced various organic EL devices using the compounds, and have extensively performed property evaluation of the devices. As a result, they have accomplished the invention.

Namely, the invention provides a compound having a pyridoindole ring structure having a substituted pyridyl group attached thereto, which is represented by the general formula (1); and an organic EL device comprising a pair of electrodes and at least one organic layer interposed between the electrodes, wherein at least one of the organic layer(s) contains the compound:

[Chem. 1]

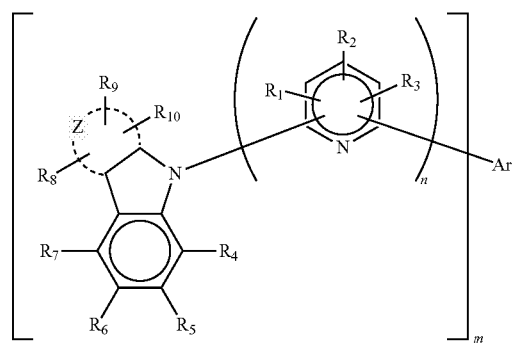

(1)

wherein Ar represents a substituted or unsubstituted aromatic hydrocarbon group, a substituted or unsubstituted aromatic heterocyclic group, or a substituted or unsubstituted condensed polycyclic aromatic group; R1 to R10 may be the same or different from one another and each independently represents a hydrogen atom, a fluorine atom, a cyano group, an alkyl group, or a substituted or unsubstituted aromatic hydrocarbon group; Z represents a 6-membered aromatic heterocyclic ring containing one nitrogen atom; and m and n each independently represents an integer of 1 to 3, provided that n is 1 when m is 2 or 3.

The aromatic hydrocarbon group, aromatic heterocyclic group or condensed polycyclic aromatic group in the substituted or unsubstituted aromatic hydrocarbon group, substituted or unsubstituted aromatic heterocyclic group, or substituted or unsubstituted condensed polycyclic aromatic group, which is represented by Ar in the general formula (1) specifically includes the following groups: a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, and an acridinyl group.

The substituent in the substituted aromatic hydrocarbon group, substituted aromatic heterocyclic group, or substituted condensed polycyclic aromatic group represented by Ar in the general formula (1) specifically includes groups such as a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

The aromatic hydrocarbon group in the substituted or unsubstituted aromatic hydrocarbon group represented by R1 to R10 in the general formula (1) specifically includes a phenyl group, a biphenyl group, a terphenyl group, a tetrakisphenyl group, a styryl group, a naphthyl group, a fluorenyl group, a phenanthryl group, an indenyl group, and a pyrenyl group.

The substituent in the substituted aromatic hydrocarbon group represented by R1 to R10 in the general formula (1) specifically includes a fluorine atom, a chlorine atom, a trifluoromethyl group, and a linear or branched alkyl group having 1 to 6 carbon atoms. These substituents may be further substituted.

The compound having a pyridoindole ring structure having a substituted pyridyl group attached thereto, which is represented by the general formula (1) of the invention, provides high electron mobility as compared with conventional electron-transporting materials, has an excellent hole-blocking ability, and is stable in a thin-film state.

The compound having a pyridoindole ring structure having a substituted pyridyl group attached thereto, which is represented by the general formula (1) of the invention, can be used as a constituent material for an electron-transporting layer of an organic EL device. Since the compound of the invention exhibits a higher electron injection/mobile rate as compared with conventional materials, the compound provides effects of improving electron transport efficiency from the electron-transporting layer to an emitting layer to enhance luminous efficiency and also lowering a driving voltage to enhance durability of the organic EL device.

The compound having a pyridoindole ring structure having a substituted pyridyl group attached thereto, which is represented by the general formula (1) of the invention, can be also used as a constituent material for a hole-blocking layer of an organic EL device. Since the compound of the invention is excellent in hole-blocking ability and also excellent in electron transport property as compared with conventional materials and has high stability in a thin-film state, the compound has provides effects of lowering a driving voltage, improving current resistance, and enhancing maximum emission luminance of the organic EL device, while exhibiting high luminous efficiency.

The compound having a pyridoindole ring structure having a substituted pyridyl group attached thereto, which is represented by the general formula (1) of the invention, can be also used as a constituent material for an emitting layer of an organic EL device. The use of an emitting layer prepared by using the compound excellent in electron transport property as compared with conventional materials and having a wide band-gap as a host material for the emitting layer and making a fluorescent material or a phosphorescent material, called a dopant, carried thereon provides an effect of realizing an organic EL device exhibiting a lowered driving voltage and having improved luminous efficiency.

Since the organic EL device of the invention uses the compound having a pyridoindole ring structure having a substituted pyridyl group attached thereto which exhibits high electron mobility as compared with conventional electron-transporting materials, has an excellent hole-blocking ability, and is stable in a thin-film state, it becomes possible to realize high efficiency and high durability.

Advantageous Effects of the Invention

The compound having a pyridoindole ring structure having a substituted pyridyl group attached thereto according to the invention is useful as a constituent material for an electron-transporting layer, a hole-blocking layer, or an emitting layer of an organic EL device and luminous efficiency and durability of a conventional organic EL device can be improved by producing an organic EL device using the compound.

DESCRIPTION OF REFERENCE NUMERALS AND SIGNS

Figure 1:
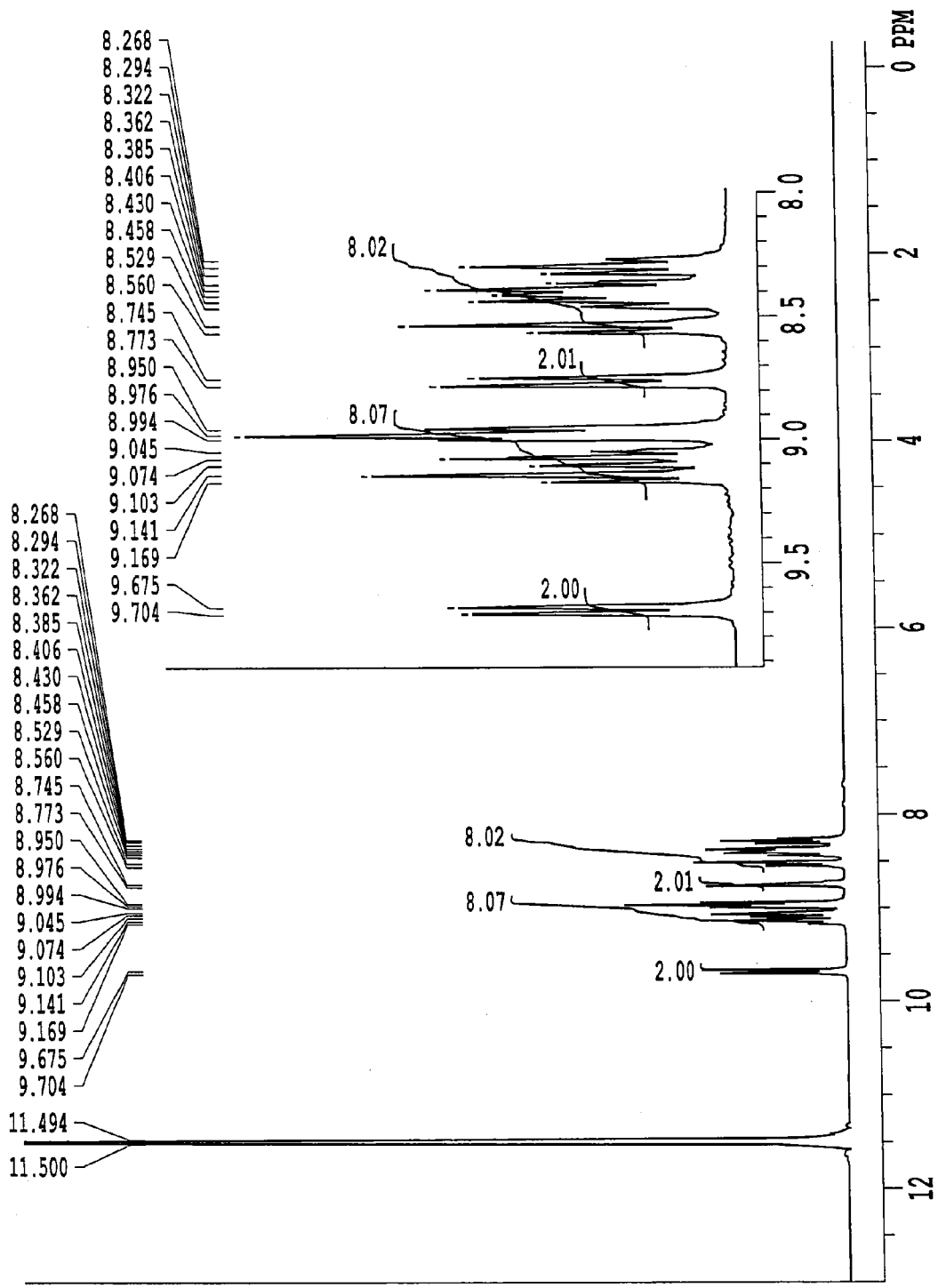
FIG. 1 is a 1H-NMR chart of the compound (Compound 2) of Invention Example 1.

1: Glass substrate
2: Transparent anode
3: Hole-injecting layer
4: Hole-transporting layer
5: Emitting layer
6: Hole-blocking layer
7: Electron-transporting layer
8: Electron-injecting layer
9: Cathode

BEST MODE FOR CARRYING OUT THE INVENTION

The compound having a pyridoindole ring structure having a substituted pyridyl group attached thereto according to the invention is a novel compound, and the compound can be synthesized, for example, by subjecting a corresponding halogenoanilinopyridine to a cyclization reaction with a palladium catalyst to synthesize a pyridoindol ring (see e.g., Non-Patent Document 5) and then by condensing it with one of various halogenopyridines to synthesize a compound having a pyridoindole ring structure having a substituted pyridyl group attached thereto.

Non-Patent Document 5: J. Chem. Soc., Perkin Trans. 1, p. 1505 (1999)

Among the compounds having a pyridoindole ring structure having a substituted pyridyl group attached thereto represented by the general formula (1), specific examples of preferred compounds are shown below, but the invention is not limited to these compounds.

[Chem. 2]

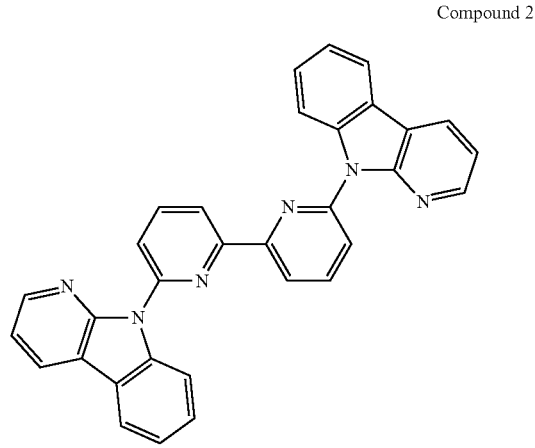

Compound 2

[Chem. 3]

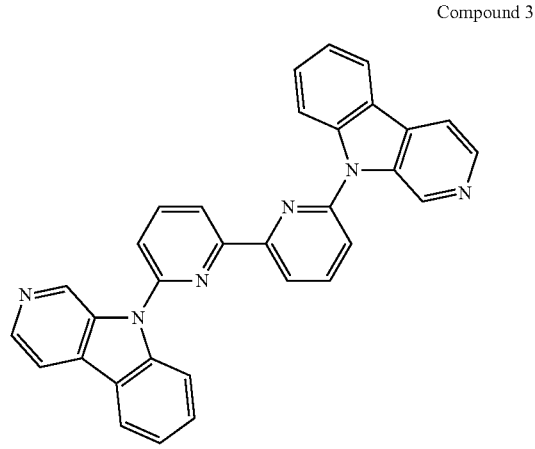

Compound 3

[Chem. 4]
Compound 4
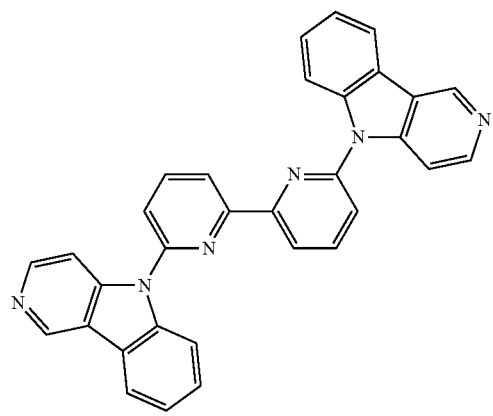
[Chem. 5]
Compound 5
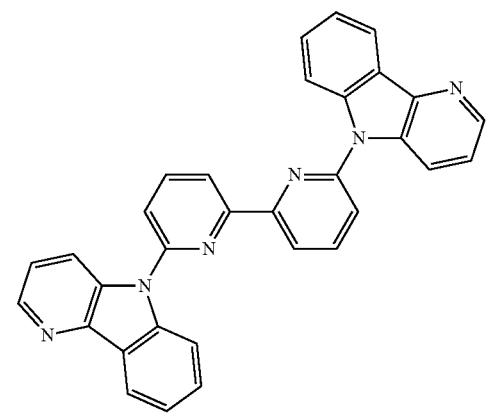
[Chem. 6]
Compound 6
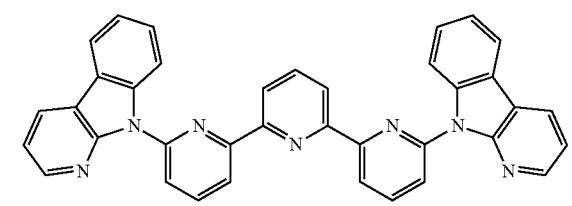
[Chem. 7]
Compound 7
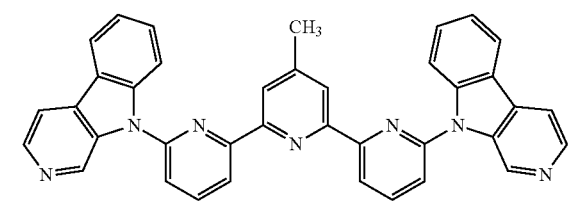
[Chem. 8]
Compound 8
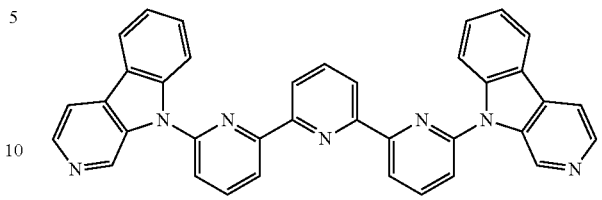
[Chem. 9]
Compound 9
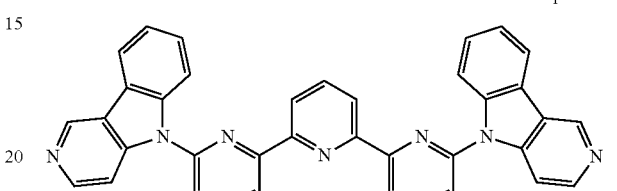
[Chem. 10]
Compound 10
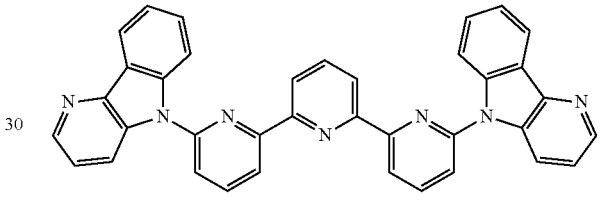
[Chem. 11]
Compound 11
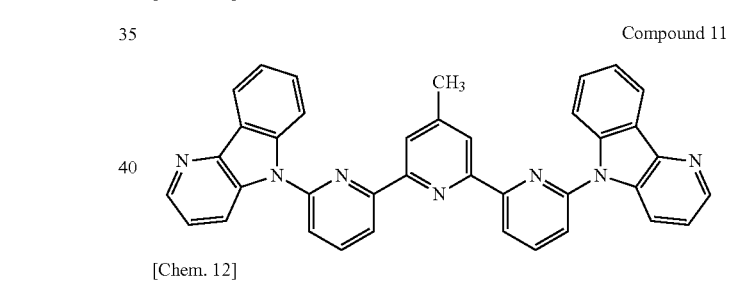
[Chem. 12]
Compound 12
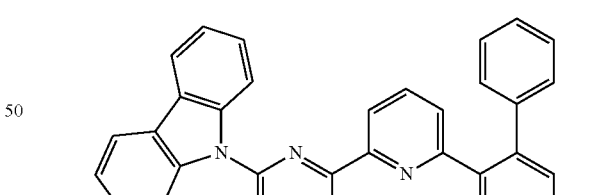
[Chem. 13]
Compound 13
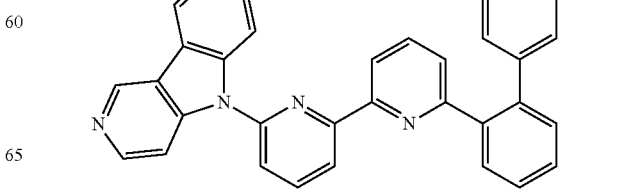

[Chem. 14]
Compound 14
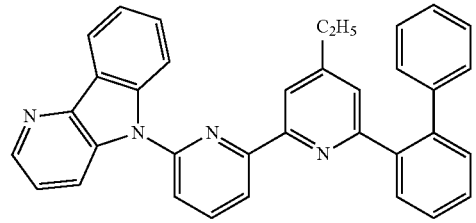
[Chem. 15]
Compound 15
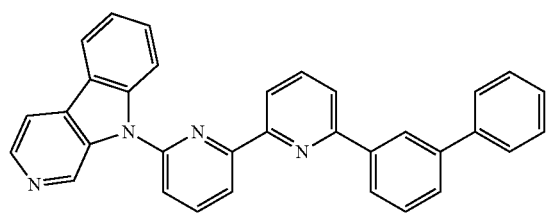
[Chem. 16]
Compound 16
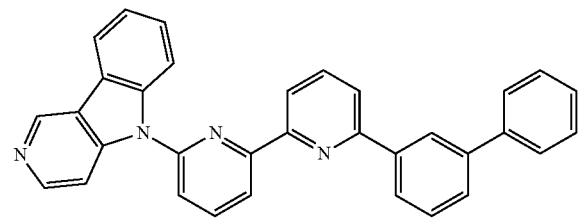
[Chem. 17]
Compound 17
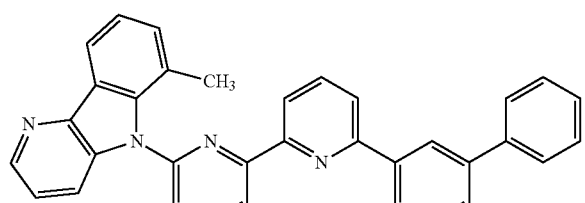
[Chem. 18]
Compound 18
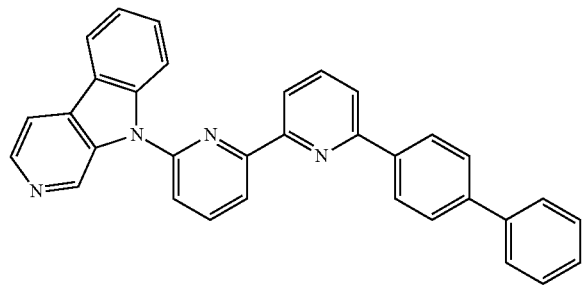
[Chem. 19]
Compound 19
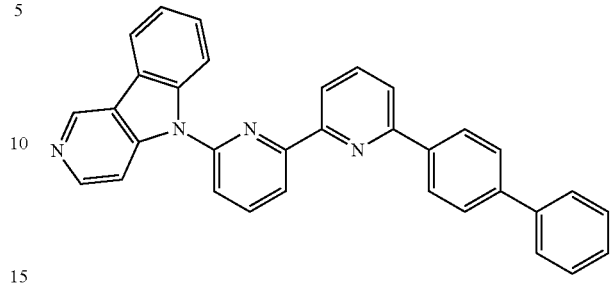
[Chem. 20]
Compound 20
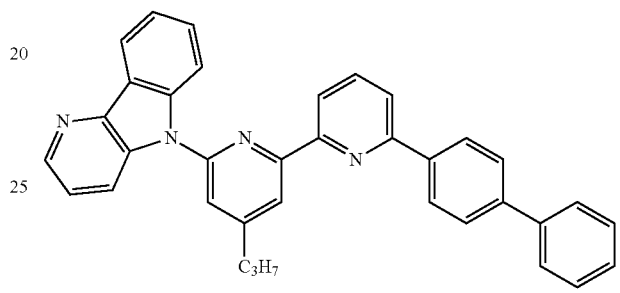
[Chem. 21]
(Compound 21)
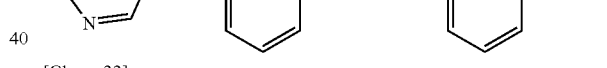
[Chem. 22]
(Compound 22)
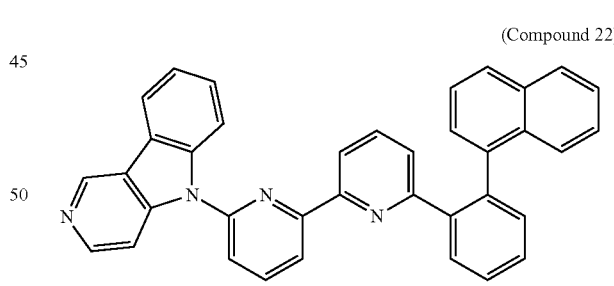
[Chem. 23]
(Compound 23)
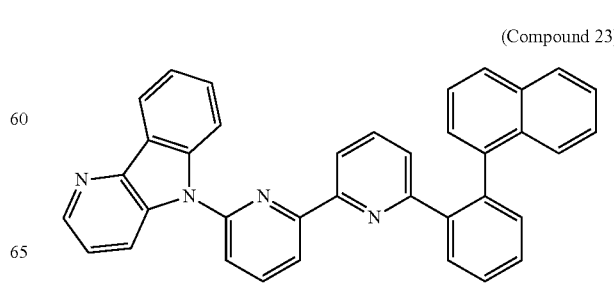

[Chem. 24]
(Compound 24)
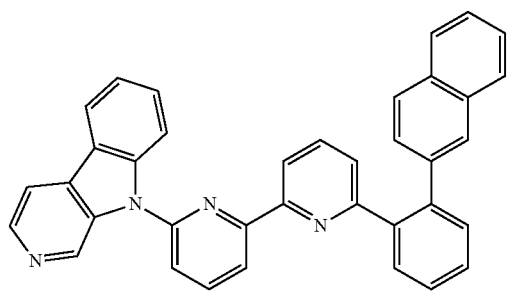
[Chem. 25]
(Compound 25)
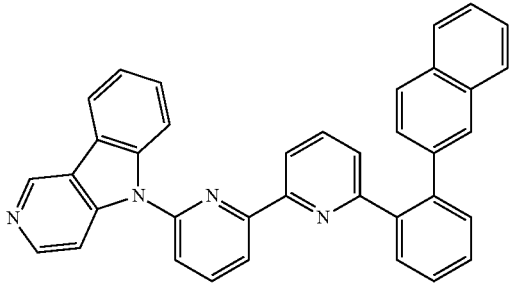
[Chem. 26]
(Compound 26)
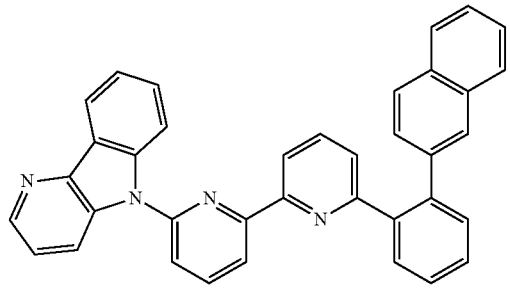
[Chem. 27]
(Compound 27)
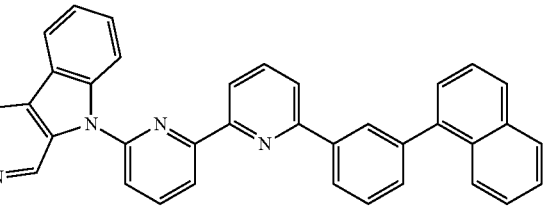
[Chem. 28]
(Compound 28)
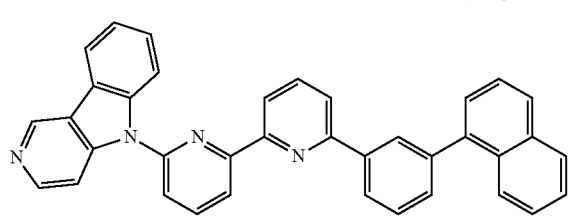
[Chem. 29]
(Compound 29)
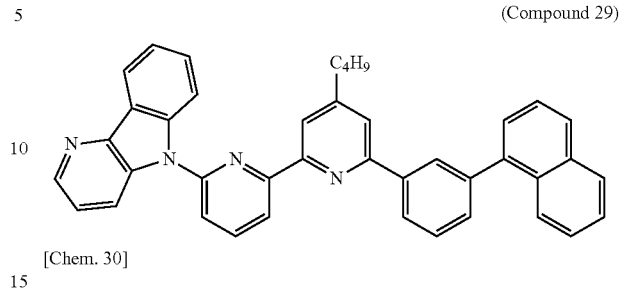
[Chem. 30]
(Compound 30)
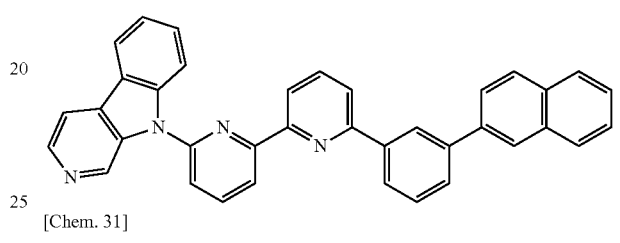
[Chem. 31]
(Compound 31)
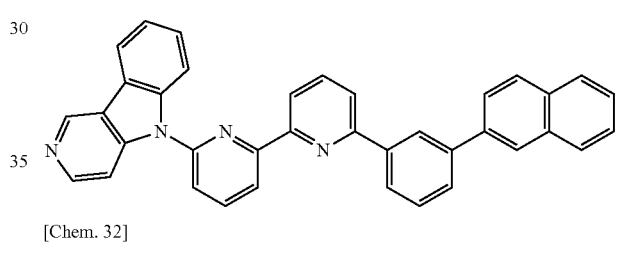
[Chem. 32]
(Compound 32)
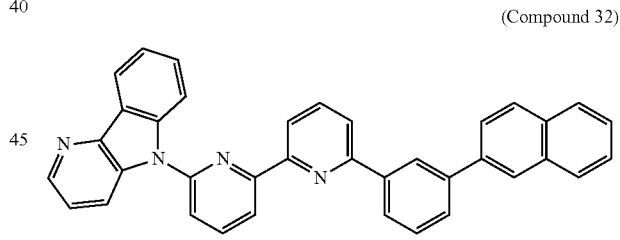
[Chem. 33]
(Compound 33)
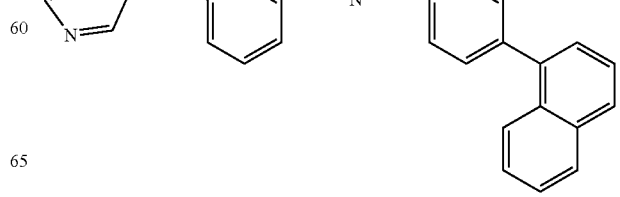

[Chem. 34]
(Compound 34)
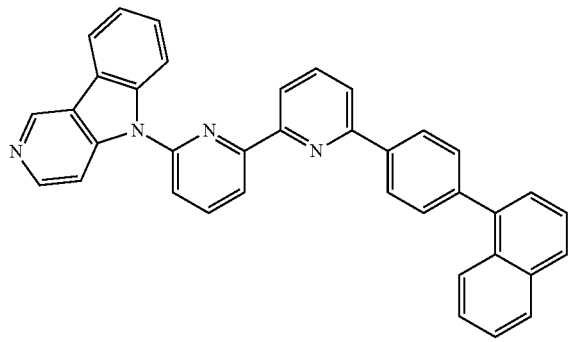
[Chem. 35]
(Compound 35)
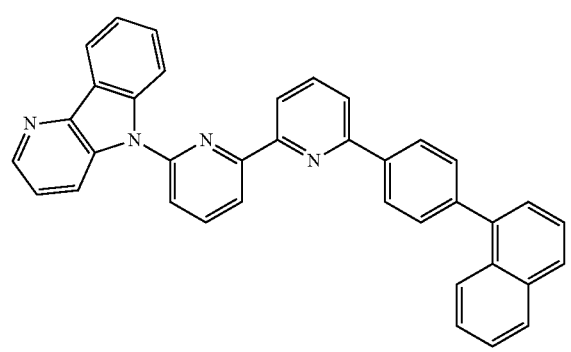
[Chem. 36]
(Compound 36)
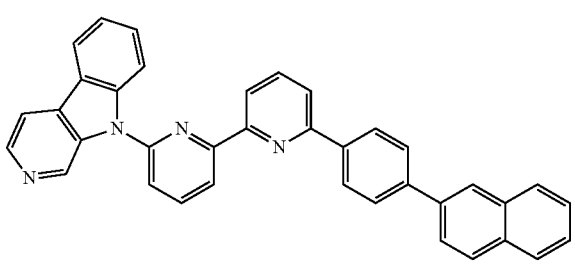
[Chem. 37]
(Compound 37)
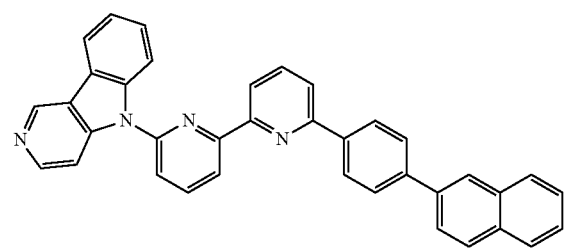
[Chem. 38]
(Compound 38)
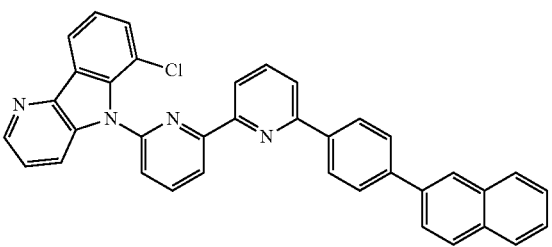
[Chem. 39]
(Compound 39)
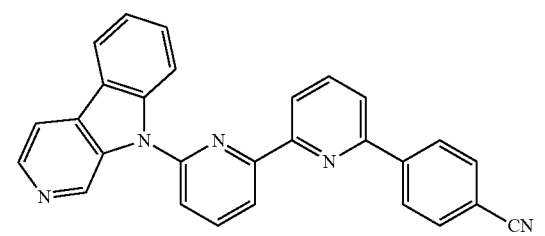
[Chem. 40]
(Compound 40)
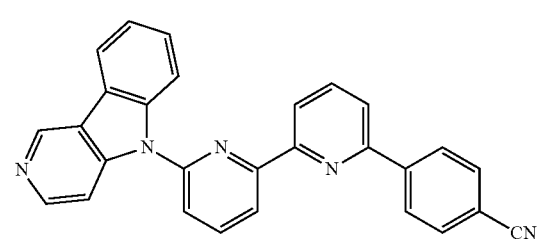
[Chem. 41]
(Compound 41)
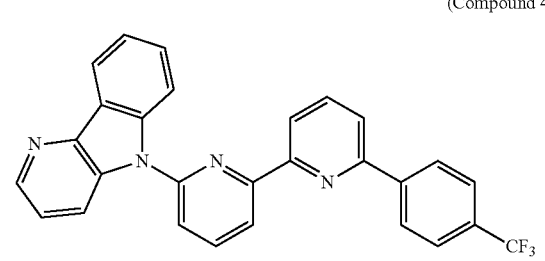
[Chem. 42]
(Compound 42)
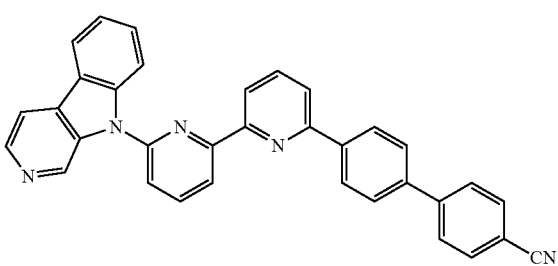

[Chem. 43]
(Compound 43)
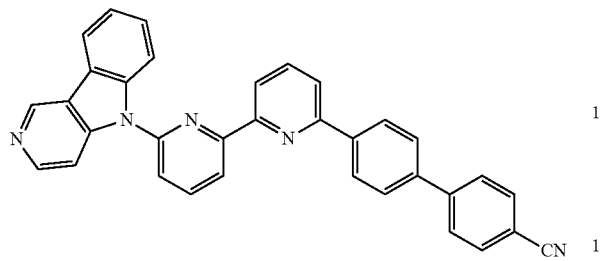
[Chem. 44]
(Compound 44)
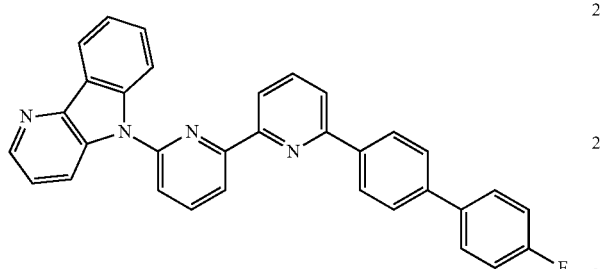
[Chem. 45]
(Compound 45)
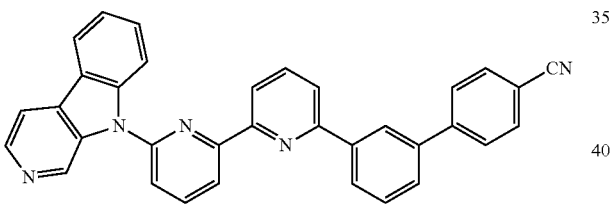
[Chem. 46]
(Compound 46)
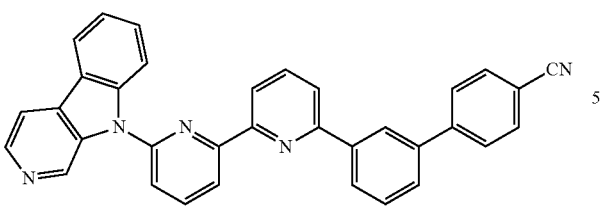
[Chem. 47]
(Compound 47)
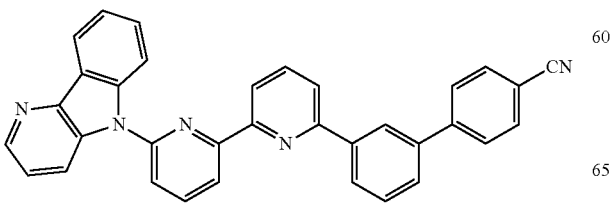
[Chem. 48]
(Compound 48)
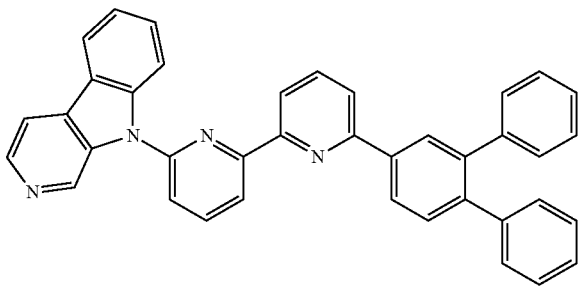
[Chem. 49]
(Compound 49)
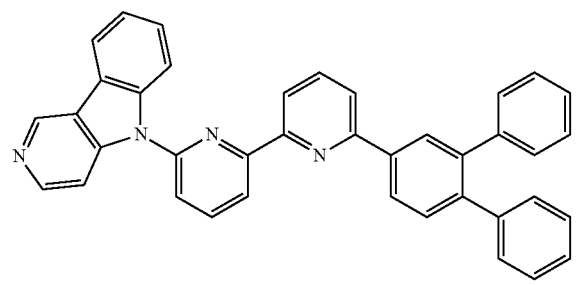
[Chem. 50]
(Compound 50)
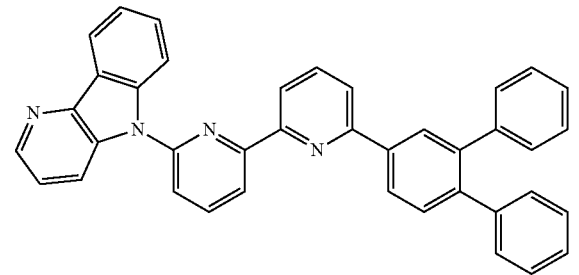
[Chem. 51]
(Compound 51)
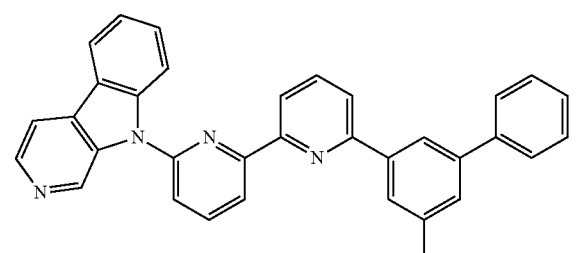

[Chem. 52]
(Compound 52)
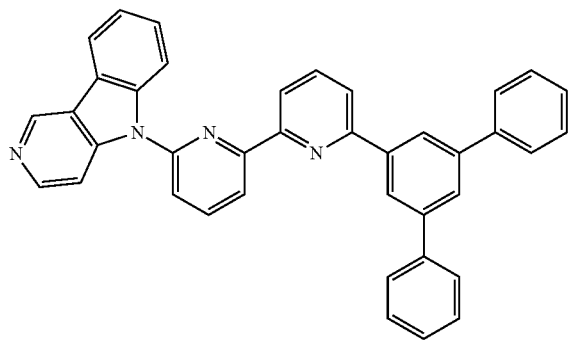
[Chem. 53]
(Compound 53)
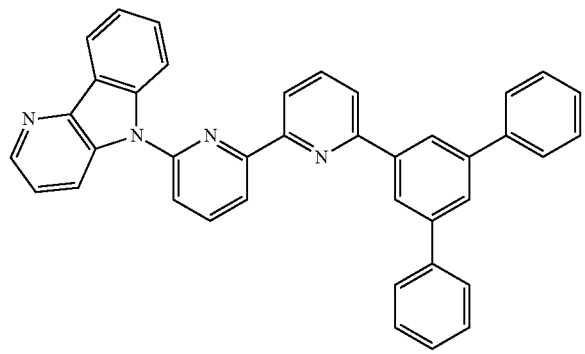
[Chem. 54]
(Compound 54)
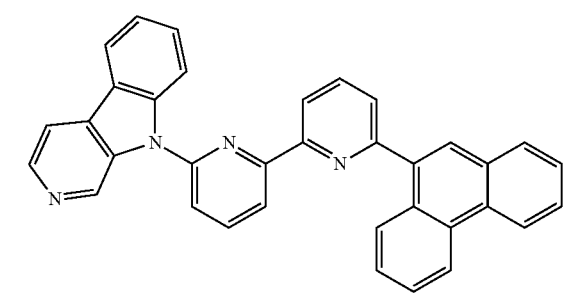
[Chem. 55]
(Compound 55)
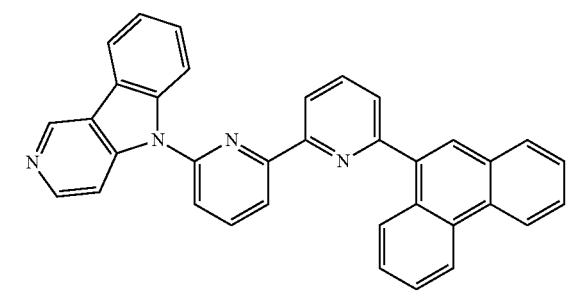
[Chem. 56]
(Compound 56)
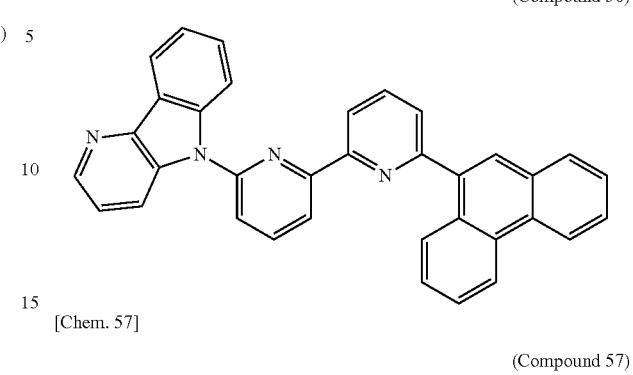
[Chem. 57]
(Compound 57)
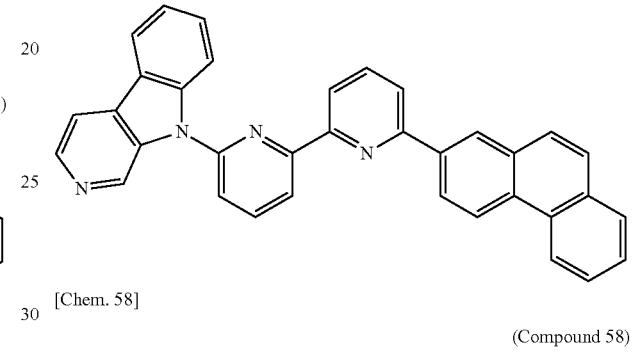
[Chem. 58]
(Compound 58)
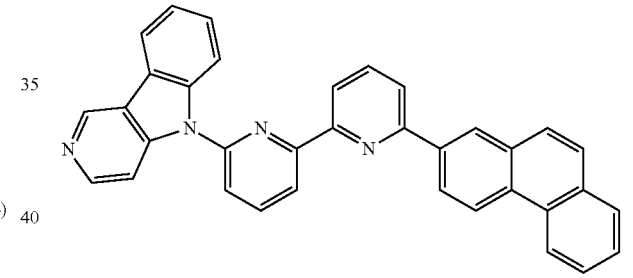
[Chem. 59]
(Compound 59)
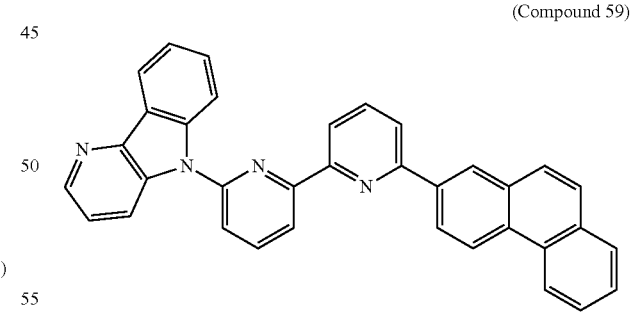
[Chem. 60]
(Compound 60)
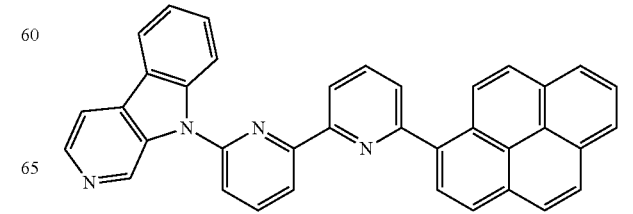

[Chem. 61]
(Compound 61)
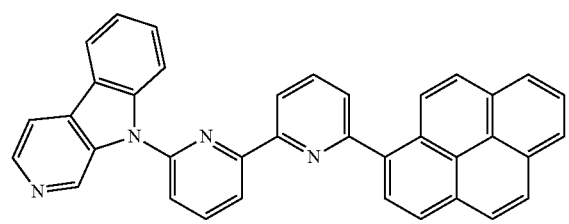
[Chem. 62]
(Compound 62)
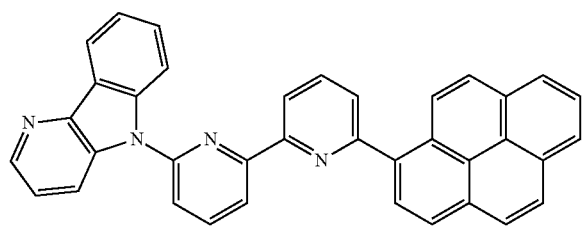
[Chem. 63]
(Compound 63)
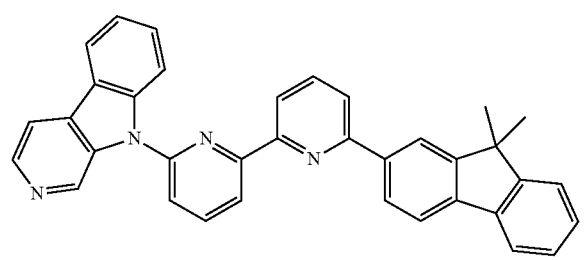
[Chem. 64]
(Compound 64)
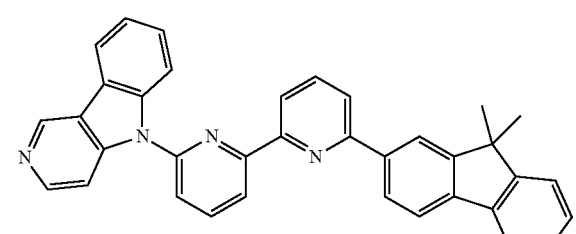
[Chem. 65]
(Compound 65)
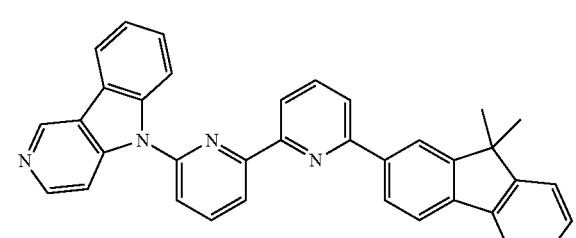
[Chem. 66]
(Compound 66)
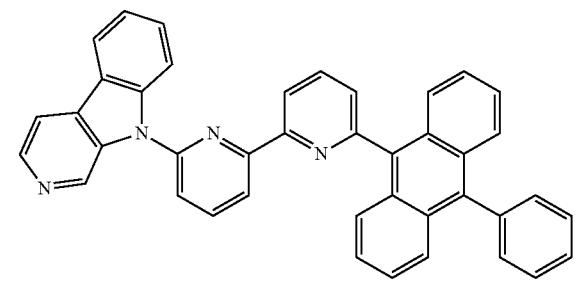
[Chem. 67]
(Compound 67)
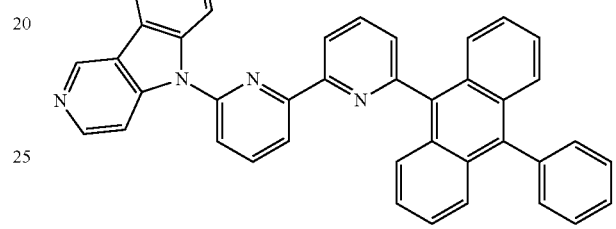
[Chem. 68]
(Compound 68)
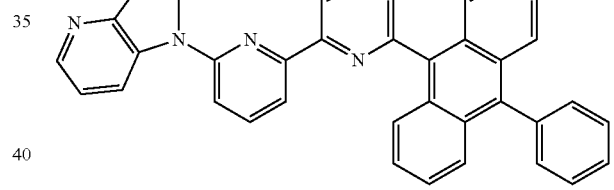
[Chem. 69]
(Compound 69)
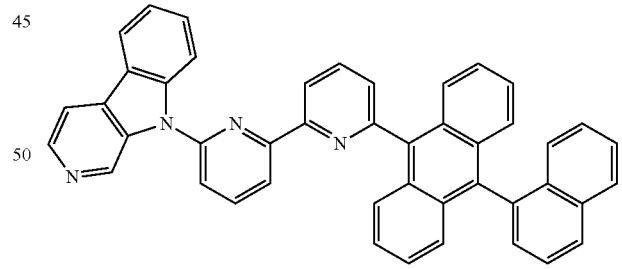
[Chem. 70]
(Compound 70)
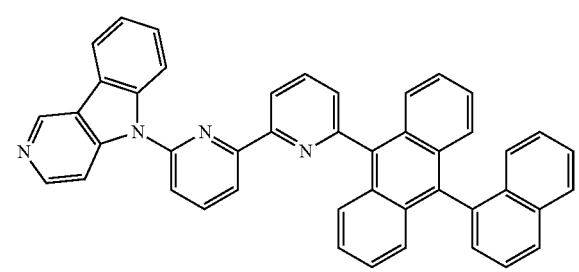

-continued
[Chem. 71]
(Compound 71)
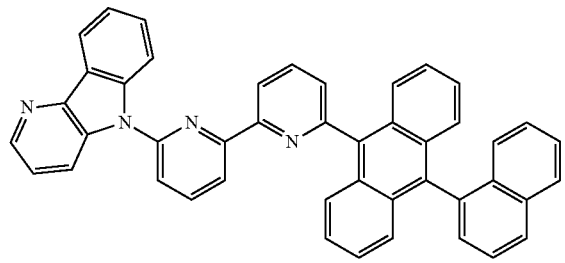
[Chem. 72]
(Compound 72)
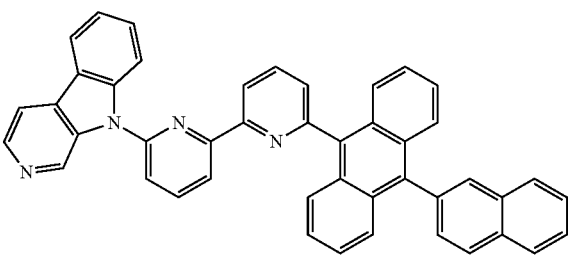
[Chem. 73]
(Compound 73)
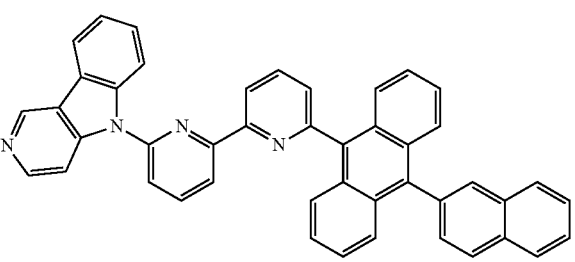
[Chem. 74]
(Compound 74)
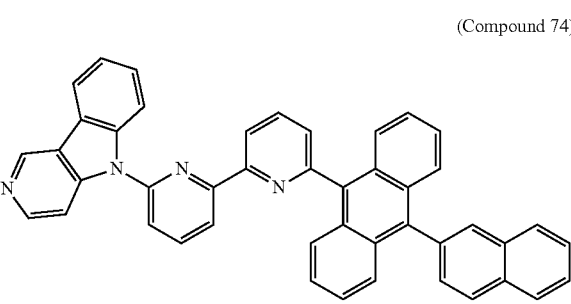
[Chem. 75]
(Compound 75)
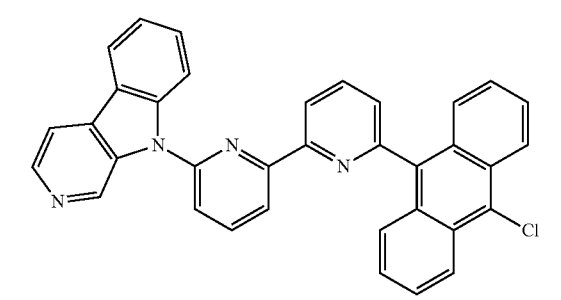
-continued
[Chem. 76]
(Compound 76)
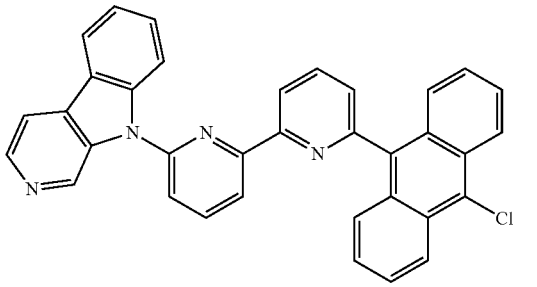
[Chem. 77]
(Compound 77)
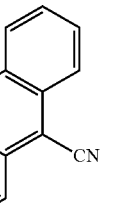
[Chem. 78]
(Compound 78)
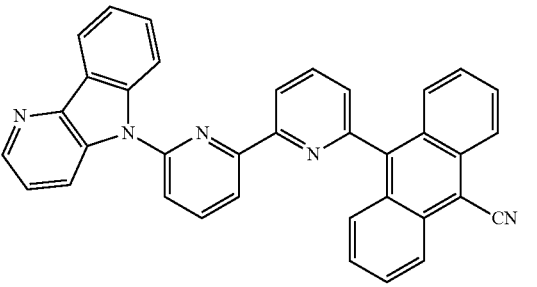
[Chem. 79]
(Compound 79)
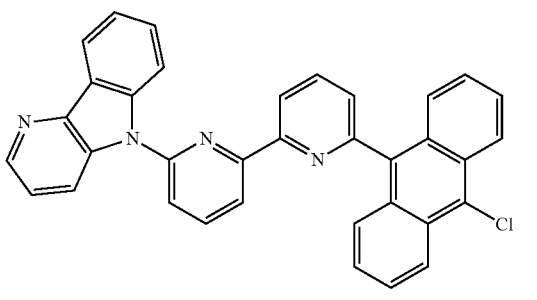

[Chem. 80]
(Compound 80)
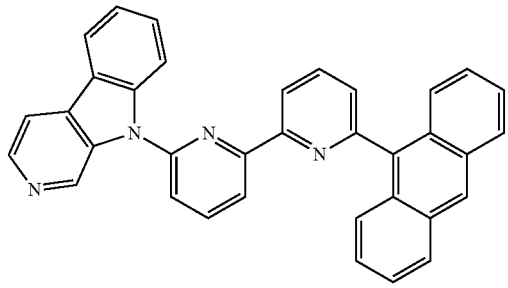
[Chem. 81]
(Compound 81)
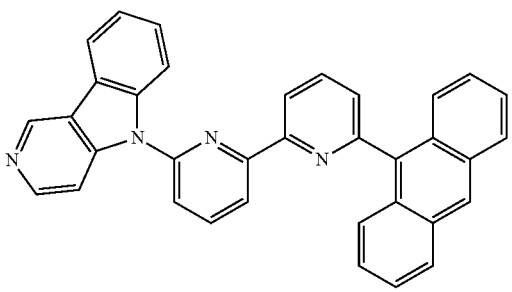
[Chem. 82]
(Compound 82)
[Chem. 83]
(Compound 83)
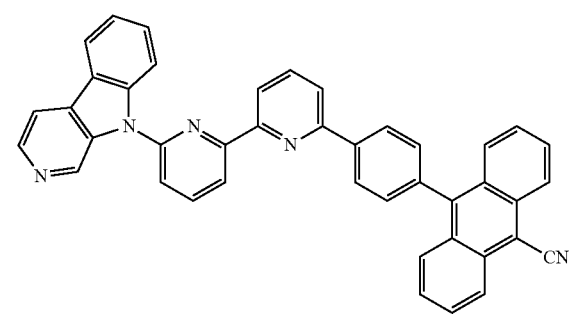
[Chem. 84]
(Compound 84)
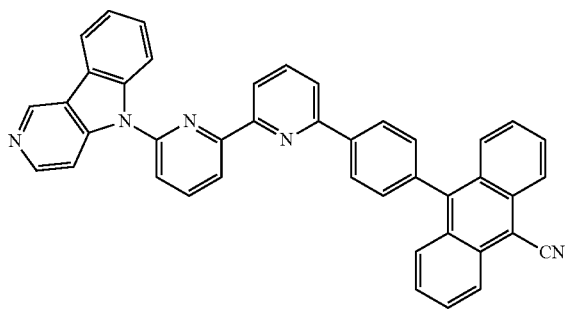
[Chem. 85]
(Compound 85)
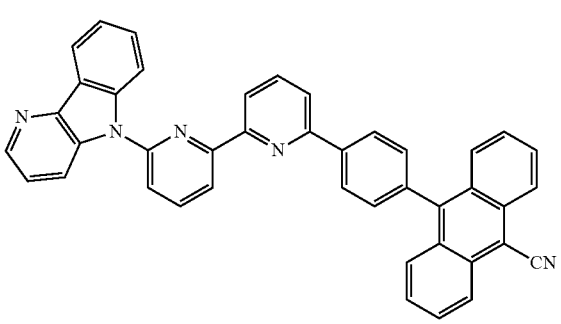
[Chem. 86]
(Compound 86)
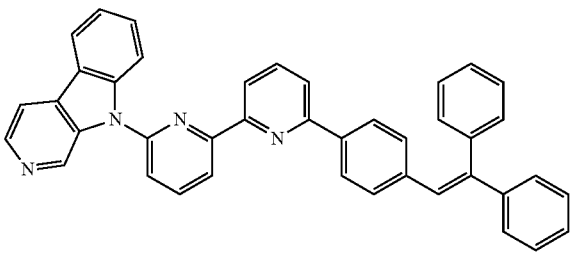
[Chem. 87]
(Compound 87)
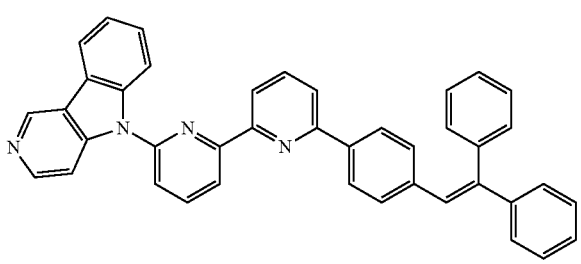

[Chem. 88]
(Compound 88)
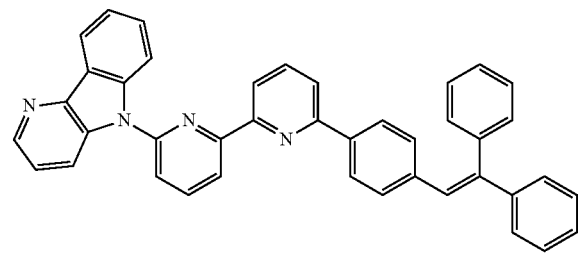
[Chem. 89]
(Compound 89)
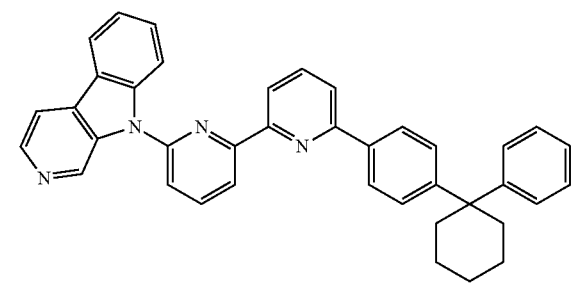
[Chem. 90]
(Compound 90)
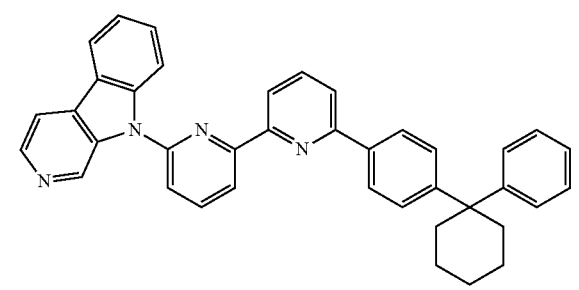
[Chem. 91]
(Compound 91)
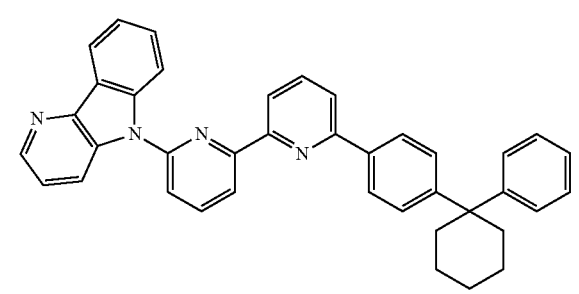
[Chem. 92]
(Compound 92)
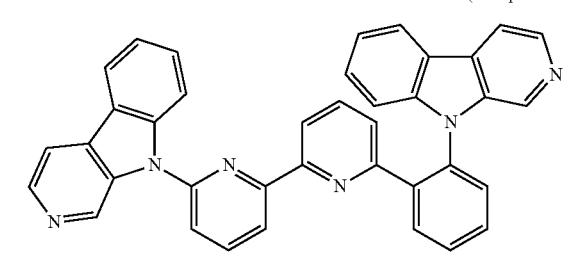
[Chem. 93]
(Compound 93)
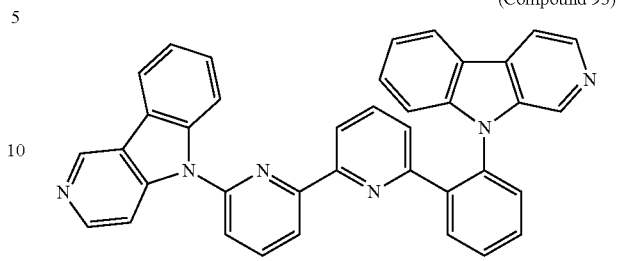
[Chem. 94]
(Compound 94)
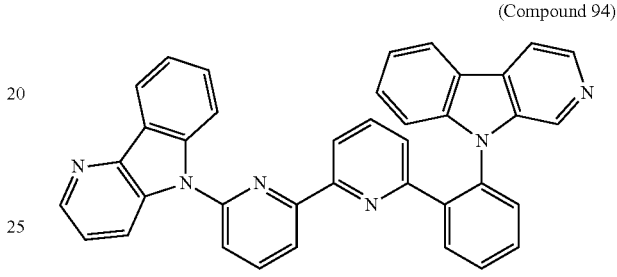
[Chem. 95]
(Compound 95)
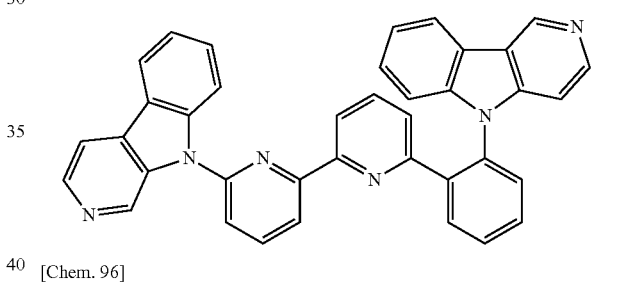
[Chem. 96]
(Compound 96)
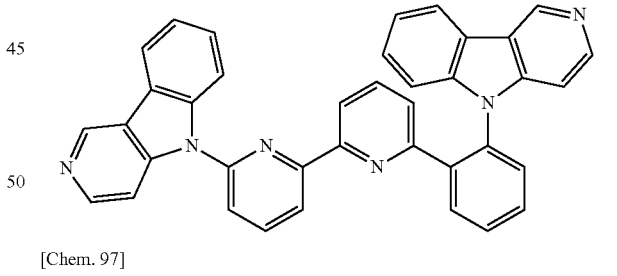
[Chem. 97]
(Compound 97)
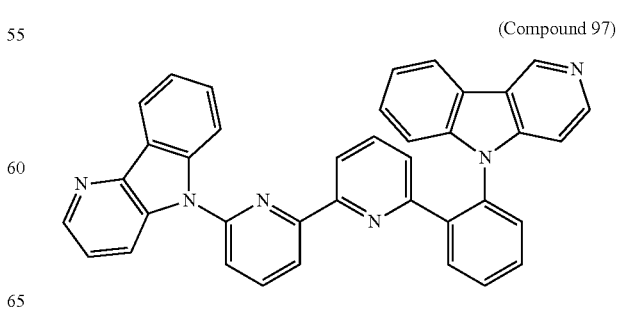

[Chem. 98]
(Compound 98)
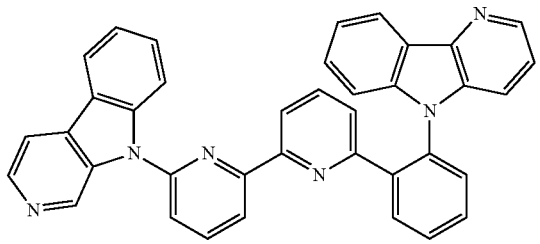
[Chem. 99]
(Compound 99)
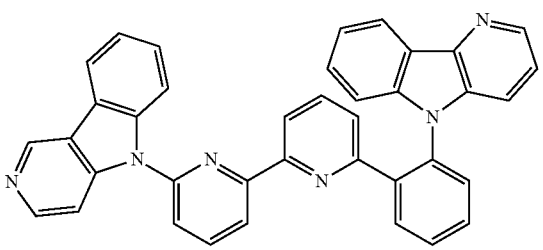
[Chem. 100]
(Compound 100)
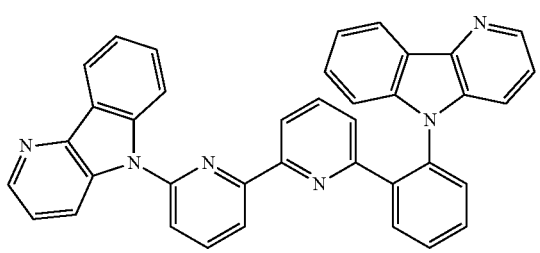
[Chem. 101]
(Compound 101)
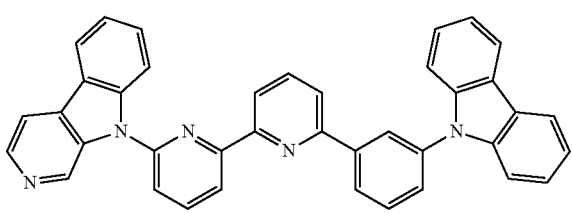
[Chem. 102]
(Compound 102)
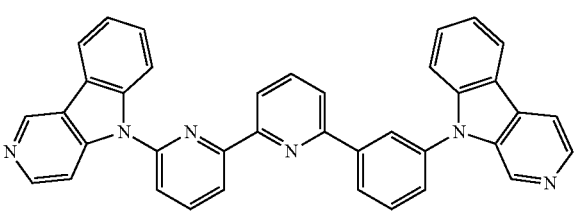
[Chem. 103]
(Compound 103)
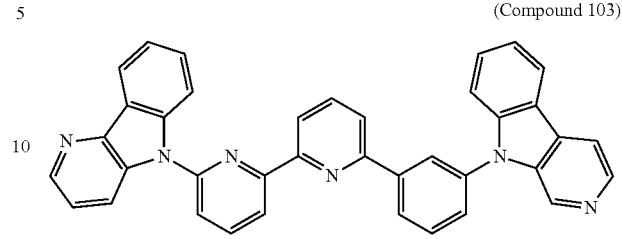
[Chem. 104]
(Compound 104)
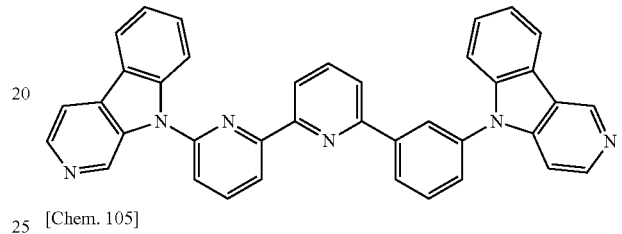
[Chem. 105]
(Compound 105)
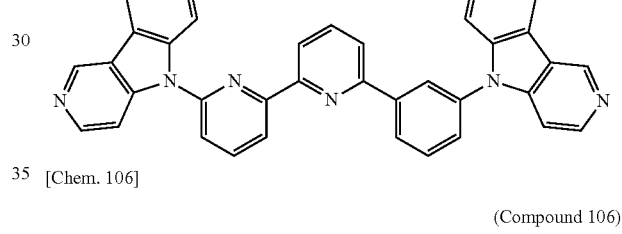
[Chem. 106]
(Compound 106)
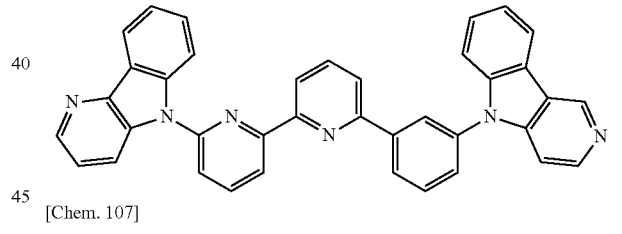
[Chem. 107]
(Compound 107)
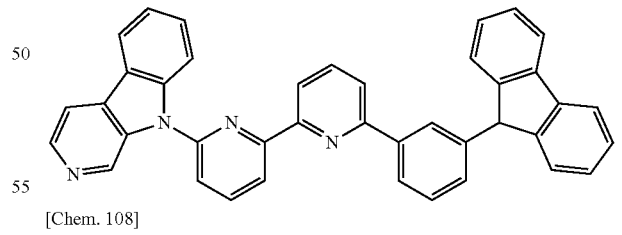
[Chem. 108]
(Compound 108)
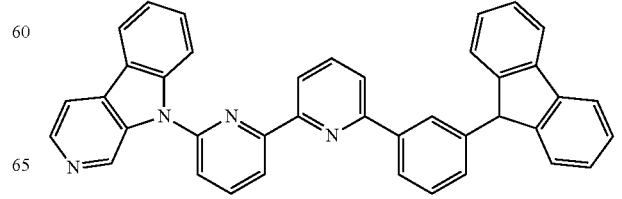

[Chem. 109]
(Compound 109)
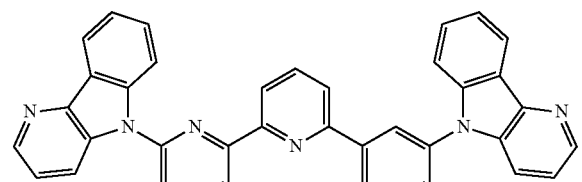
[Chem. 110]
(Compound 110)
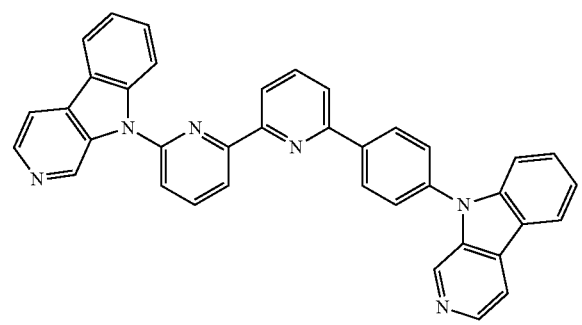
[Chem. 111]
(Compound 111)
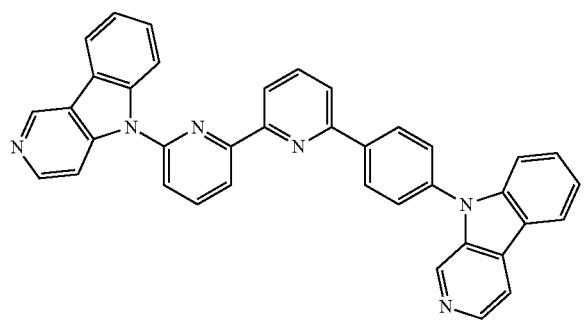
[Chem. 112]
(Compound 112)
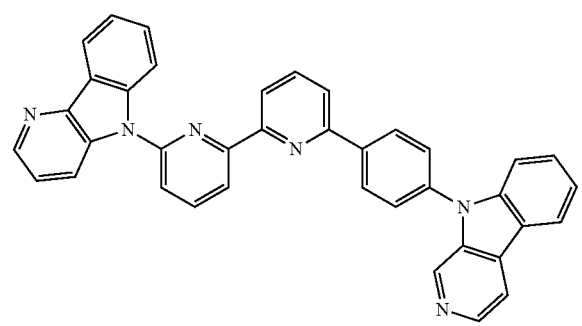
[Chem. 113]
(Compound 113)
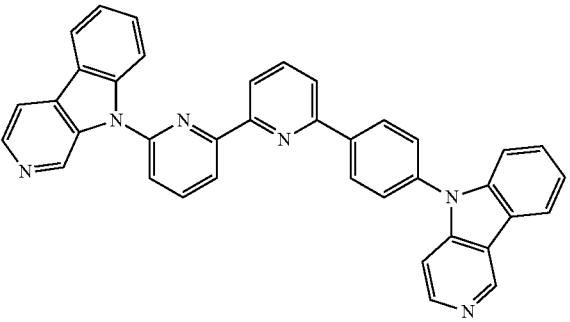
[Chem. 114]
(Compound 114)
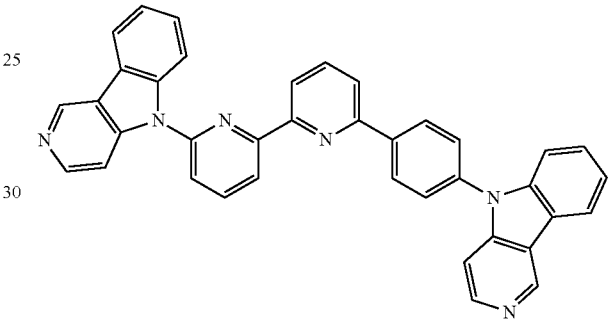
[Chem. 115]
(Compound 115)
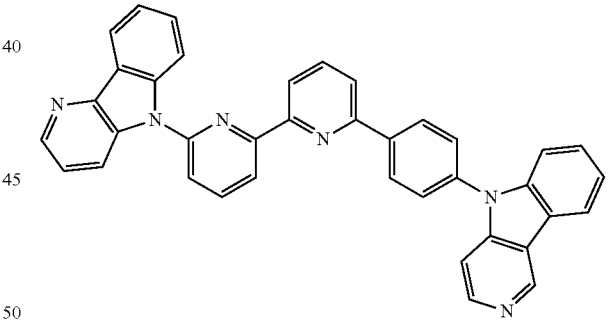
[Chem. 116]
(Compound 116)
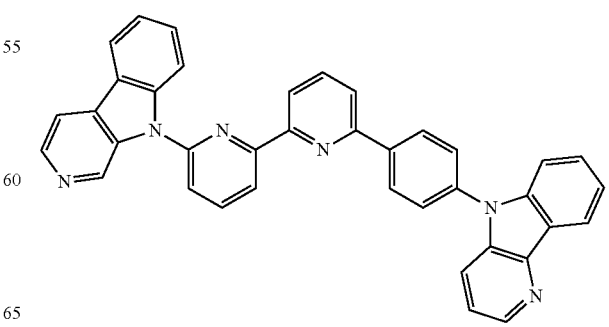

[Chem. 117]
(Compound 117)
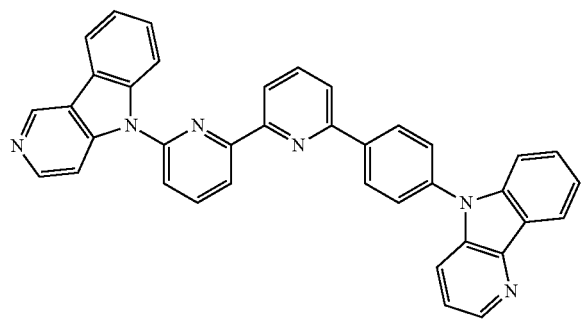
[Chem. 118]
(Compound 118)
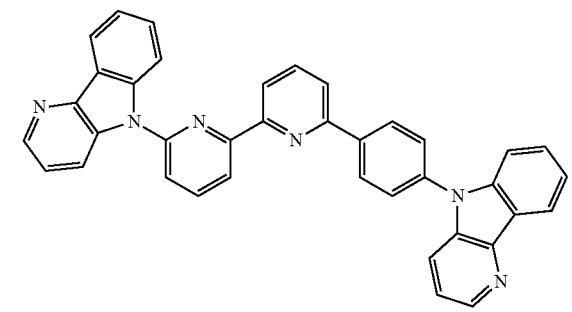
[Chem. 119]
(Compound 119)
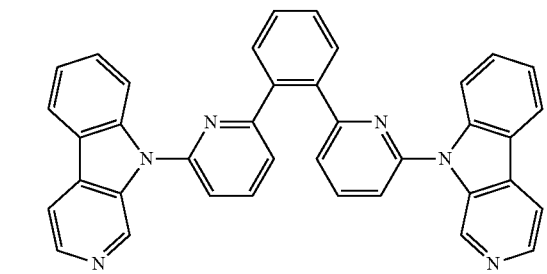
[Chem. 120]
(Compound 120)
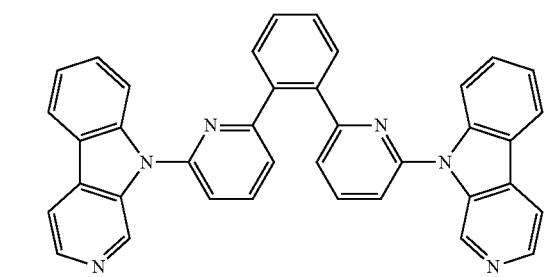
[Chem. 121]
(Compound 121)
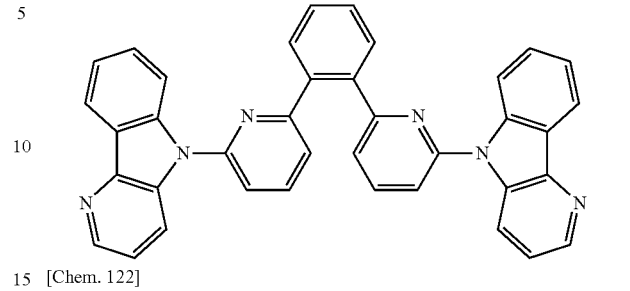
[Chem. 122]
(Compound 122)
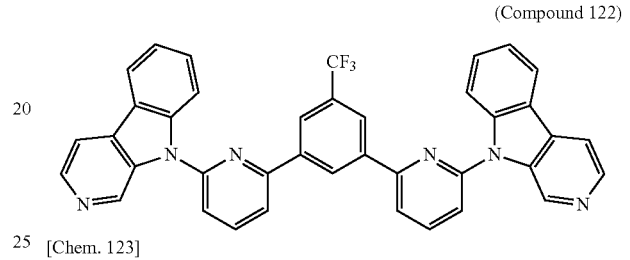
[Chem. 123]
(Compound 123)
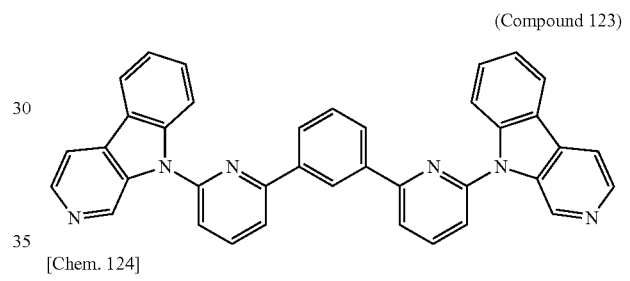
[Chem. 124]
(Compound 124)
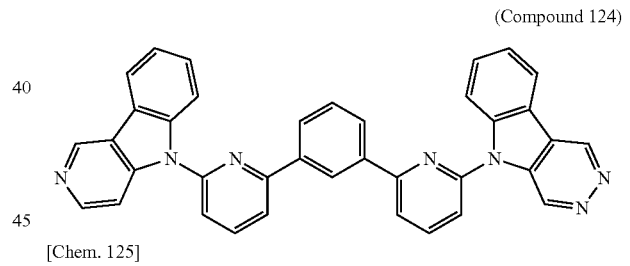
[Chem. 125]
(Compound 125)
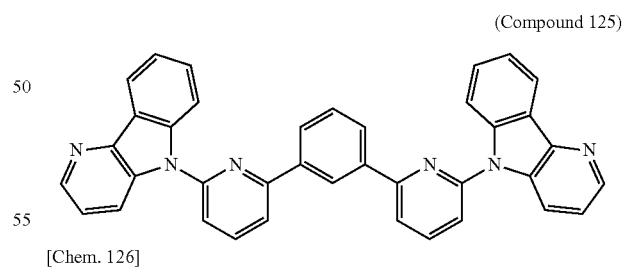
[Chem. 126]
(Compound 126)
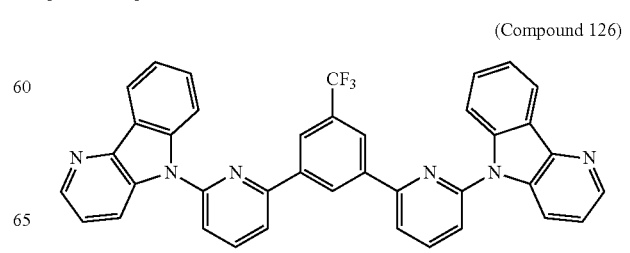

[Chem. 127]
(Compound 127)
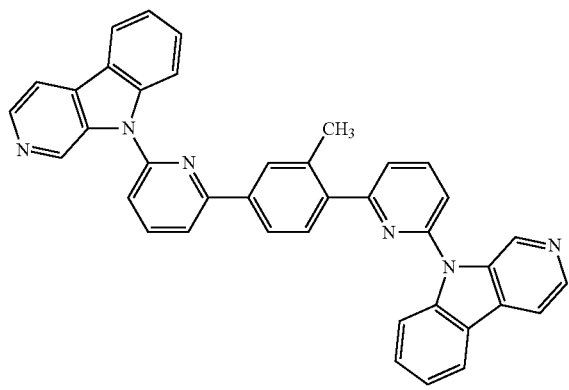
[Chem. 128]
(Compound 128)
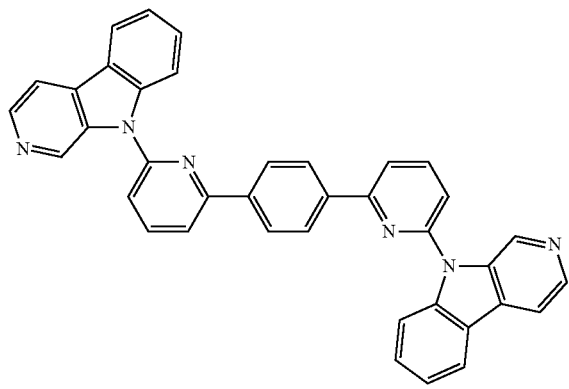
[Chem. 129]
(Compound 129)
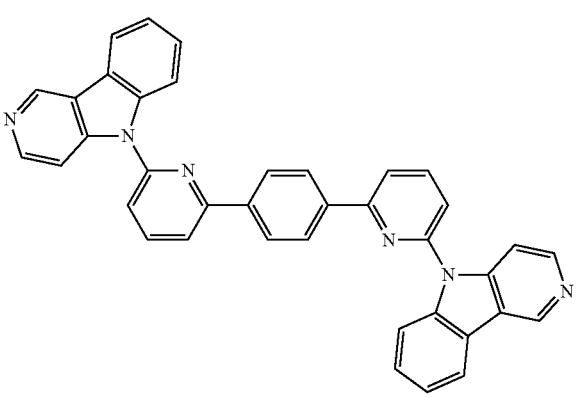
[Chem. 130]
(Compound 130)
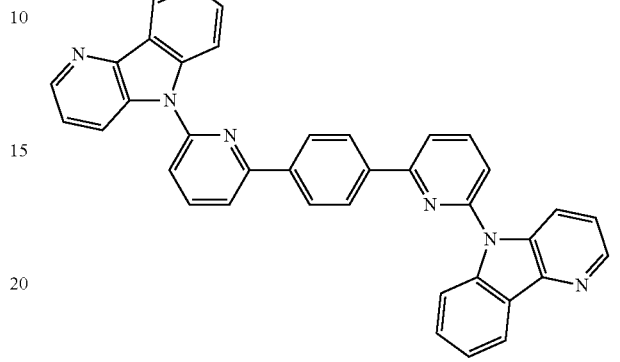
[Chem. 131]
(Compound 131)
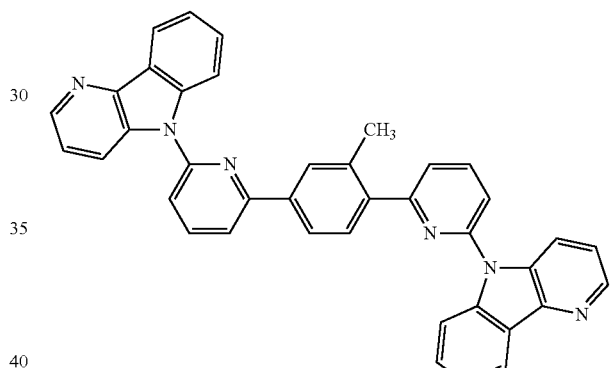
[Chem. 132]
(Compound 132)
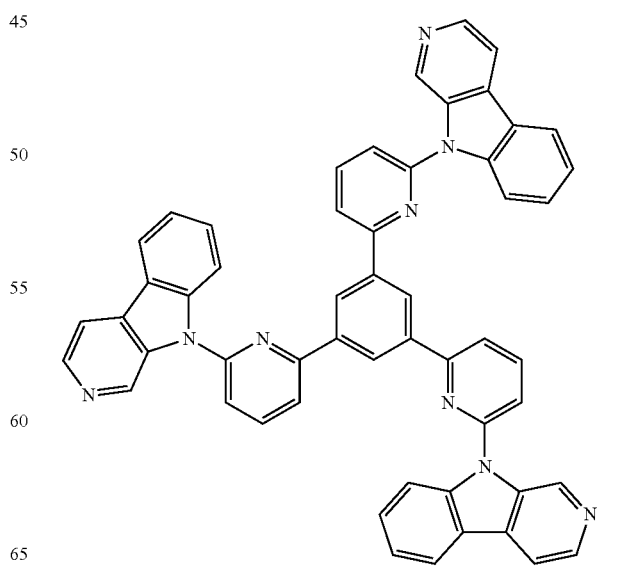

[Chem. 133]
(Compound 133)
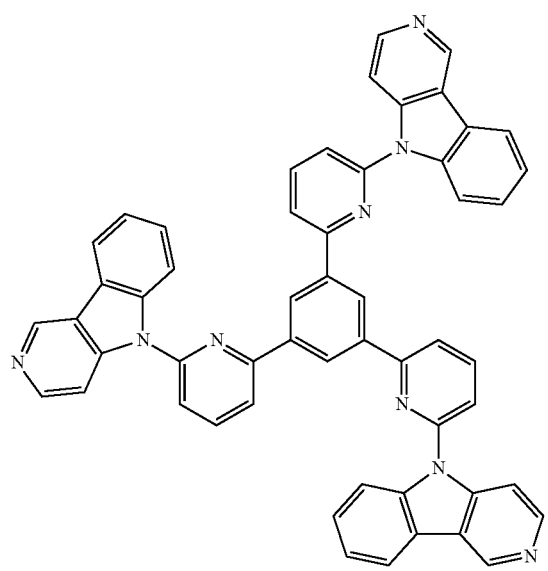
[Chem. 134]
(Compound 134)
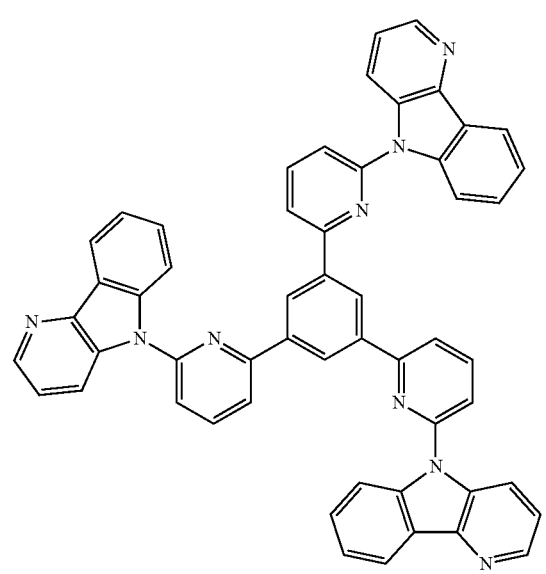
[Chem. 135]
(Compound 135)
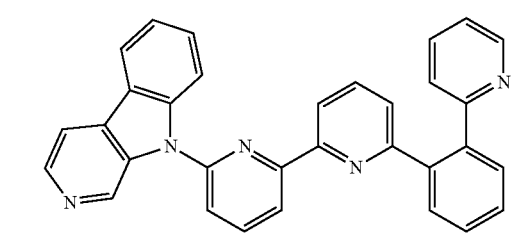
[Chem. 136]
(Compound 136)
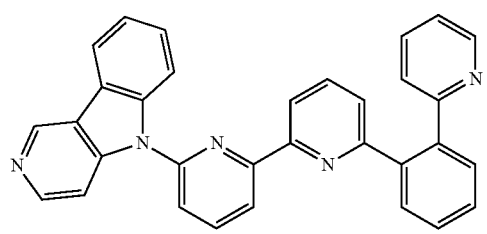
[Chem. 137]
(Compound 137)
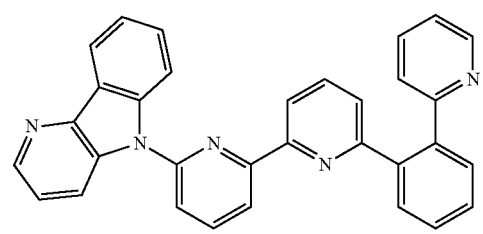
[Chem. 138]
(Compound 138)
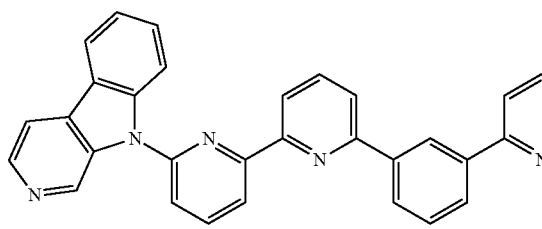
[Chem. 139]
(Compound 139)
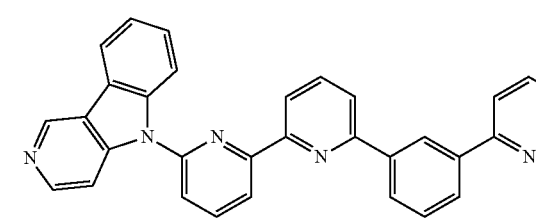
[Chem. 140]
(Compound 140)
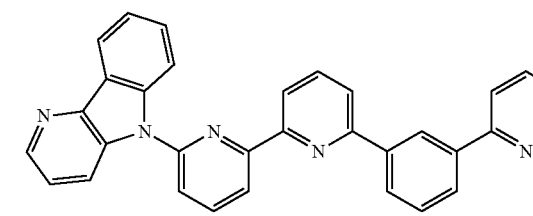

[Chem. 141]
(Compound 141)
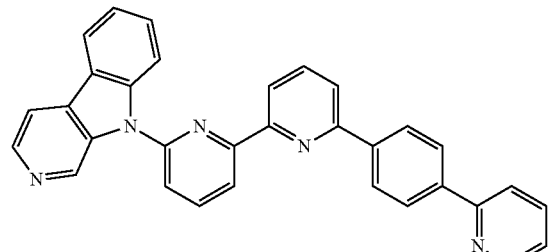
[Chem. 142]
(Compound 142)
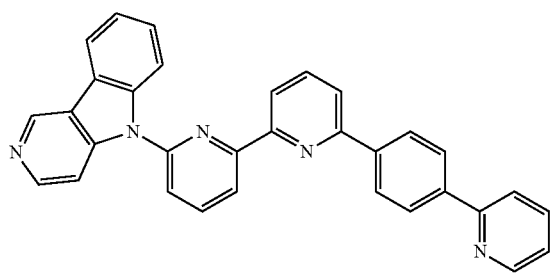
[Chem. 143]
(Compound 143)
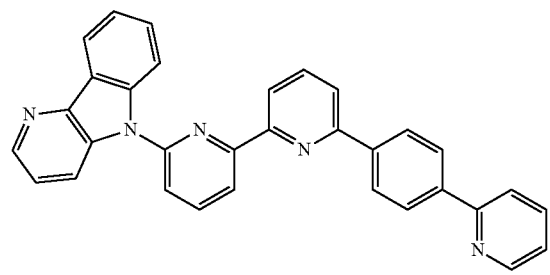
[Chem. 144]
(Compound 144)
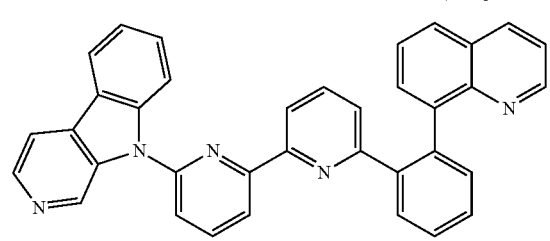
[Chem. 145]
(Compound 145)
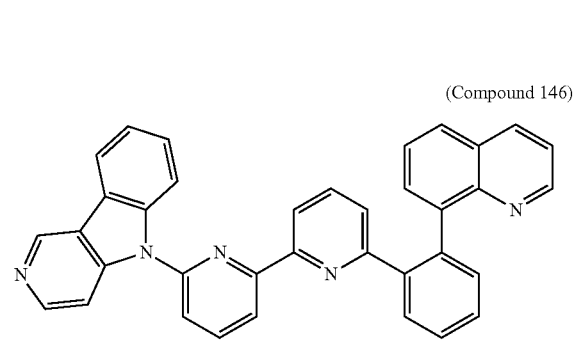
[Chem. 146]
(Compound 146)
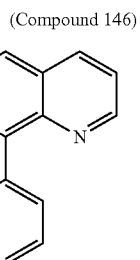
[Chem. 147]
(Compound 147)
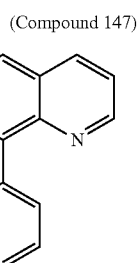
[Chem. 148]
(Compound 148)
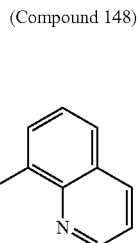
[Chem. 149]
(Compound 149)
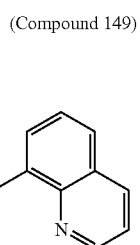
[Chem. 150]
(Compound 150)
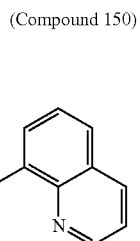

[Chem. 151]
(Compound 151)
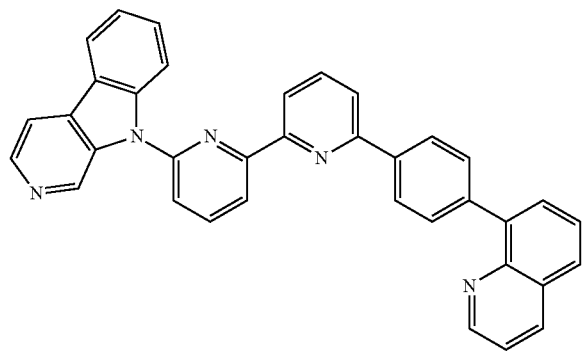
[Chem. 152]
(Compound 152)
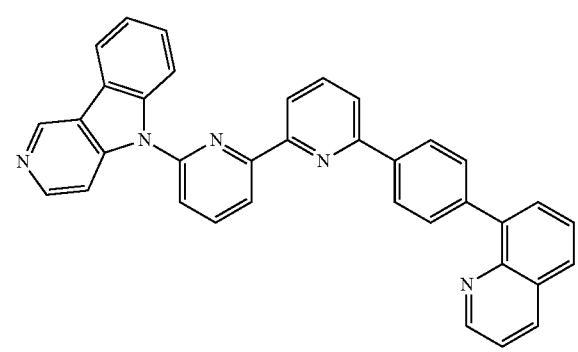
[Chem. 152]
(Compound 152)
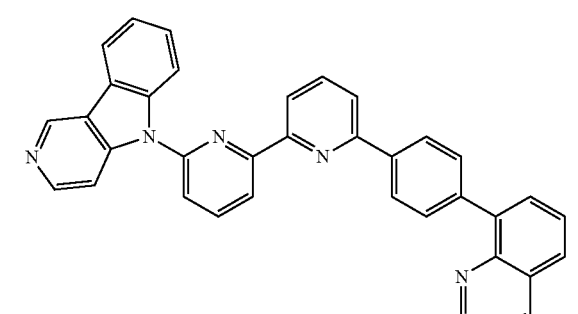
[Chem. 153]
(Compound 153)
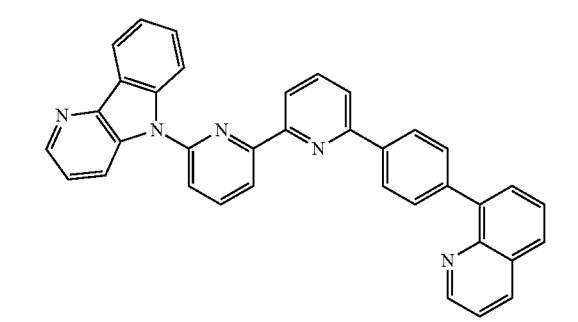
[Chem. 154]
(Compound 154)
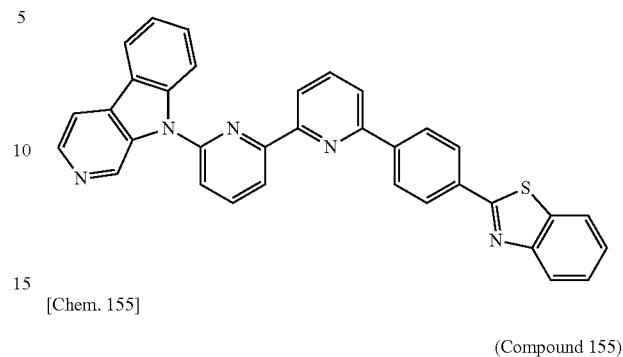
[Chem. 155]
(Compound 155)
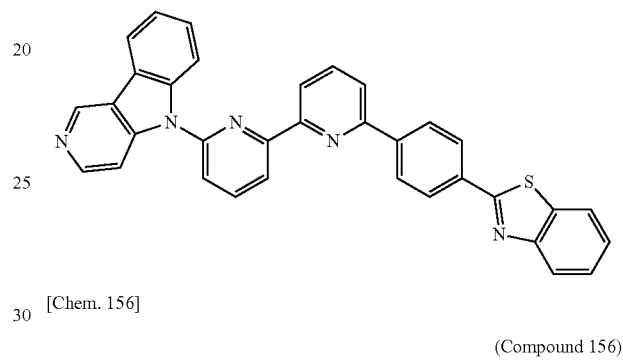
[Chem. 156]
(Compound 156)
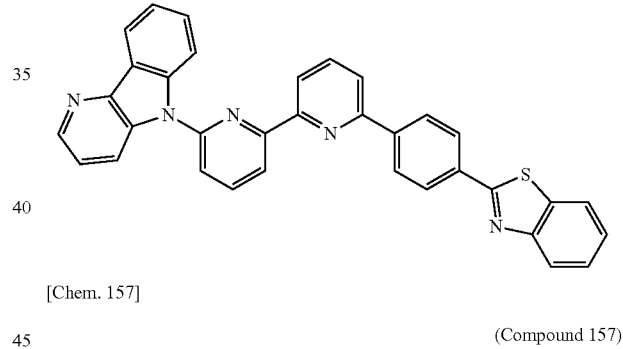
[Chem. 157]
(Compound 157)
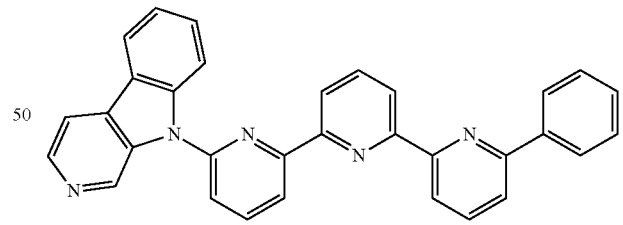
[Chem. 158]
(Compound 158)
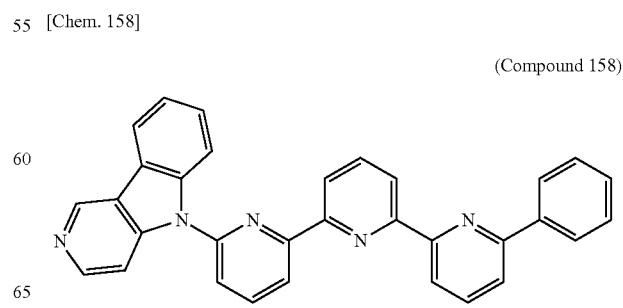

[Chem. 159]
(Compound 159)
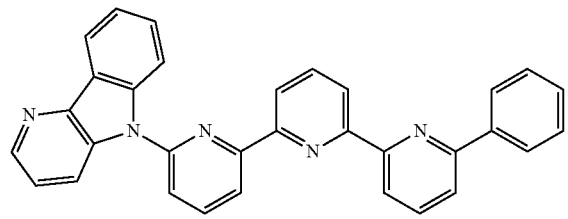
[Chem. 160]
(Compound 160)
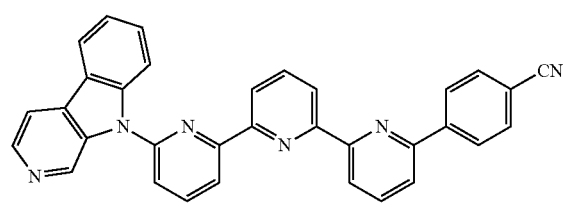
[Chem. 161]
(Compound 161)
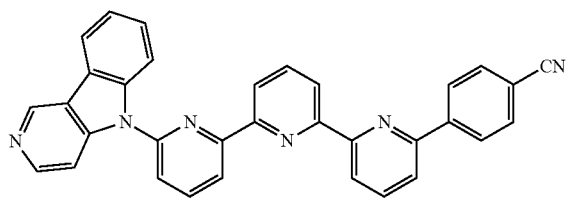
[Chem. 162]
(Compound 162)
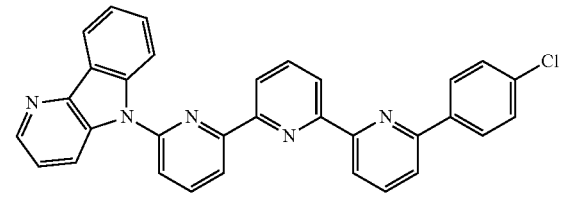
[Chem. 163]
(Compound 163)
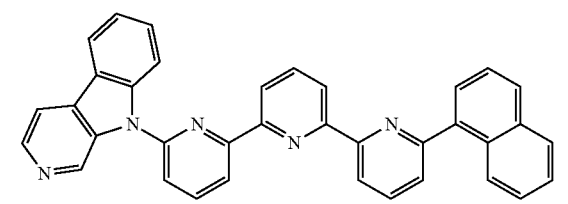
[Chem. 164]
(Compound 164)
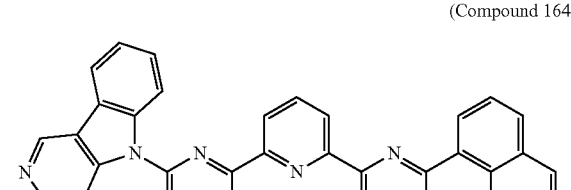
[Chem. 165]
(Compound 165)
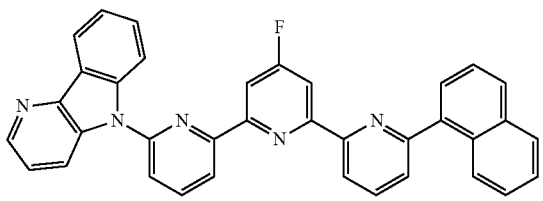
[Chem. 166]
(Compound 166)
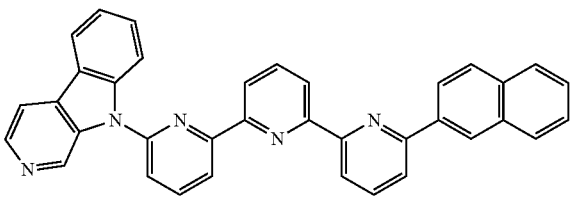
[Chem. 167]
(Compound 167)
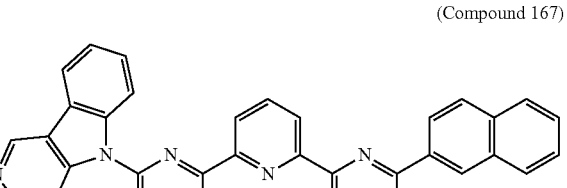
[Chem. 168]
(Compound 168)
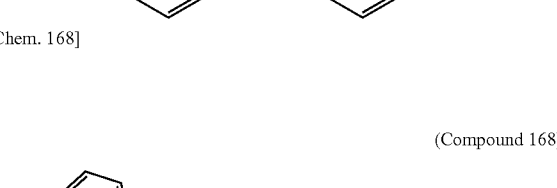
[Chem. 169]
(Compound 169)
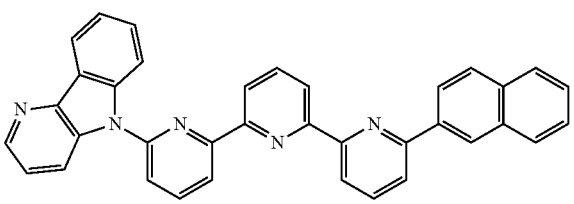
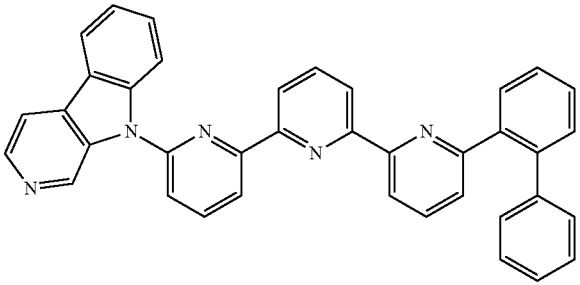

[Chem. 170]
(Compound 170)
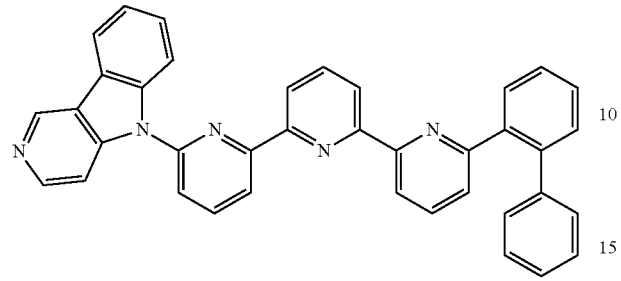
[Chem. 171]
(Compound 171)
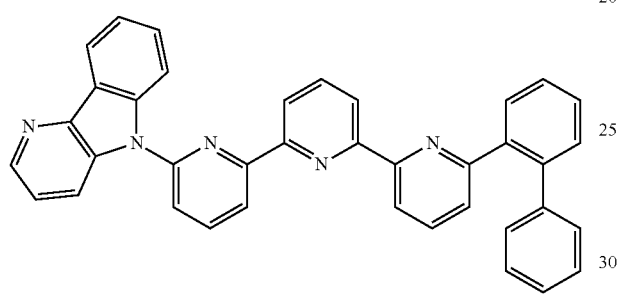
[Chem. 172]
(Compound 172)
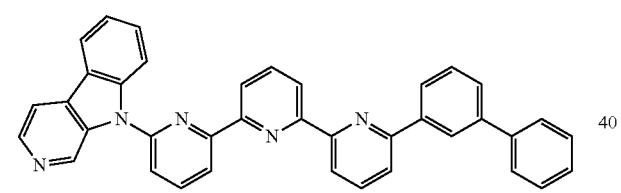
[Chem. 173]
(Compound 173)
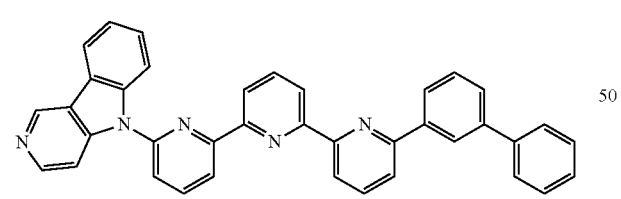
[Chem. 174]
(Compound 174)
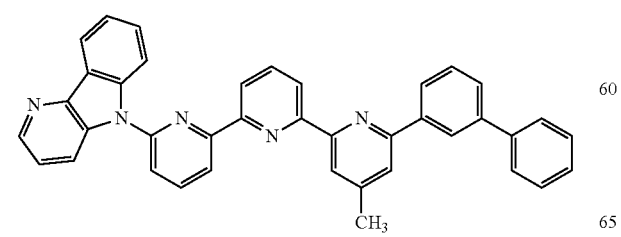
[Chem. 175]
(Compound 175)
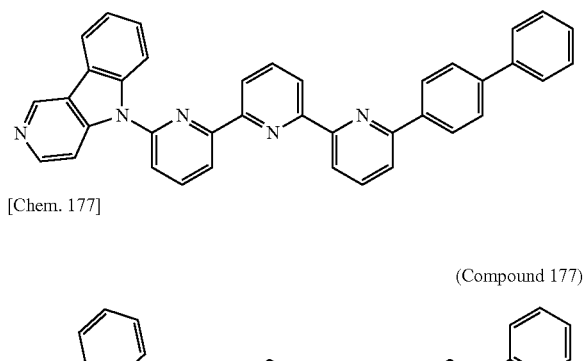
[Chem. 176]
(Compound 176)
[Chem. 177]
(Compound 177)
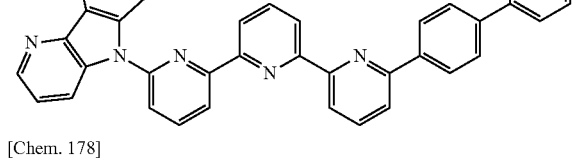
[Chem. 178]
(Compound 178)
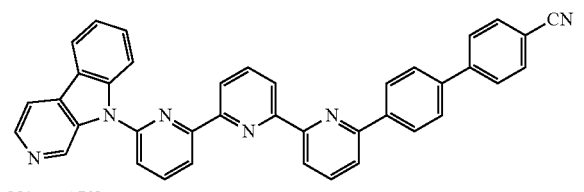
[Chem. 179]
(Compound 179)
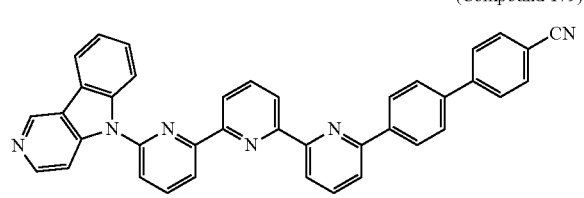
[Chem. 180]
(Compound 180)
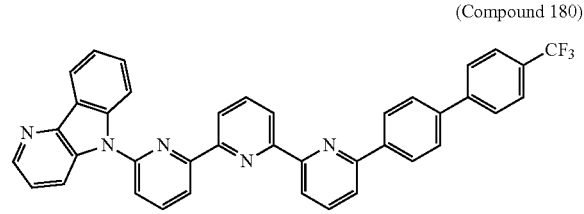

[Chem. 181]
(Compound 181)
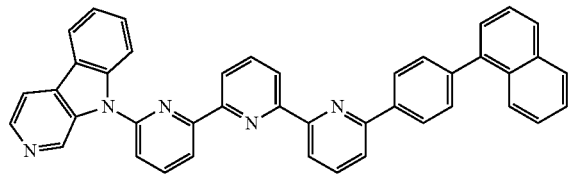
[Chem. 182]
(Compound 182)
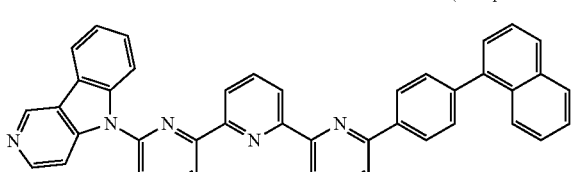
[Chem. 183]
(Compound 183)
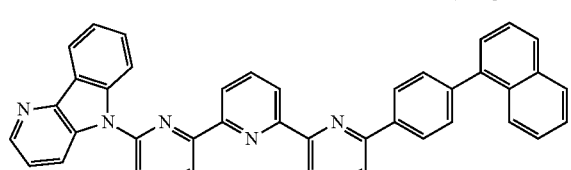
[Chem. 184]
(Compound 184)
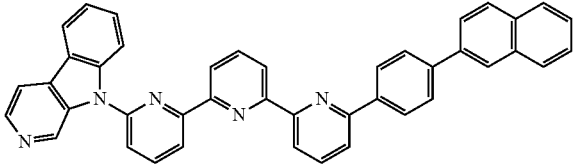
[Chem. 185]
(Compound 185)
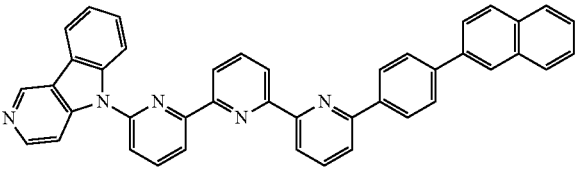
[Chem. 186]
(Compound 186)
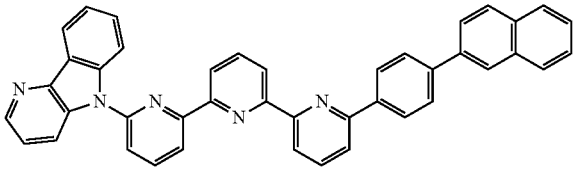
[Chem. 187]
(Compound 187)
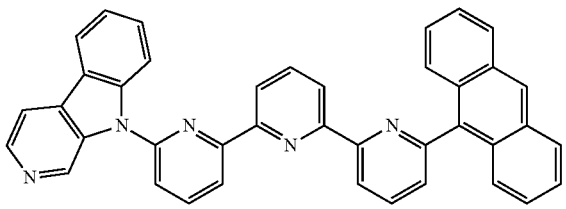
[Chem. 188]
(Compound 188)
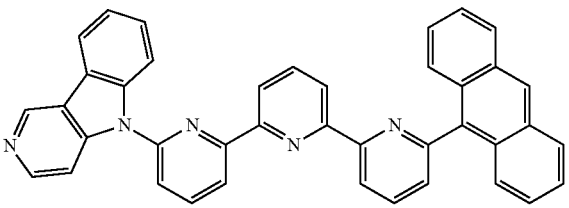
[Chem. 189]
(Compound 189)
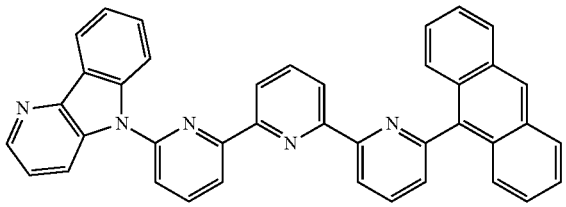
[Chem. 190]
(Compound 190)
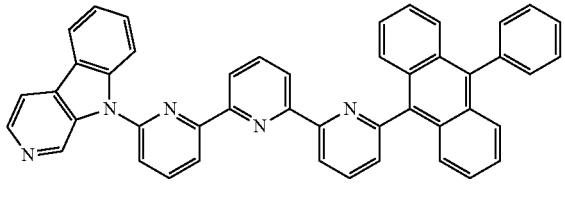
[Chem. 191]
(Compound 191)
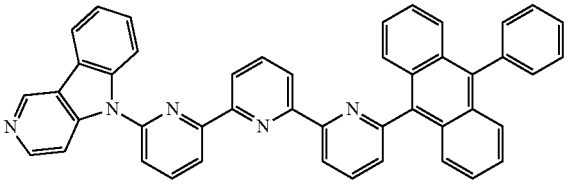
[Chem. 192]
(Compound 192)
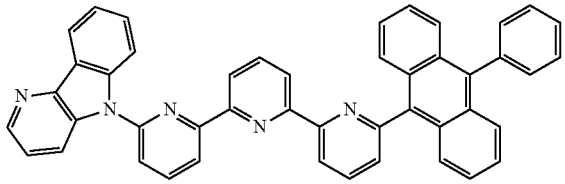

[Chem. 193]
(Compound 193)
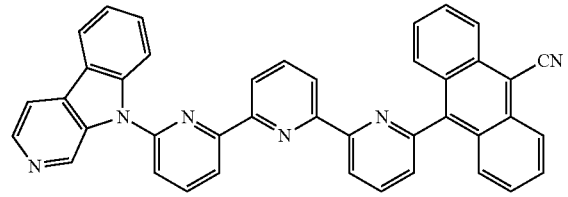
[Chem. 194]
(Compound 194)
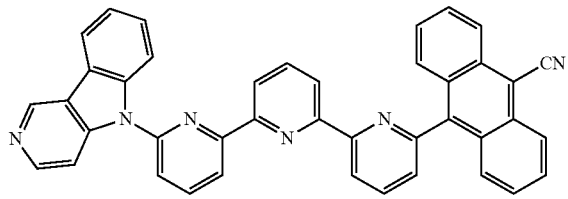
[Chem. 195]
(Compound 195)
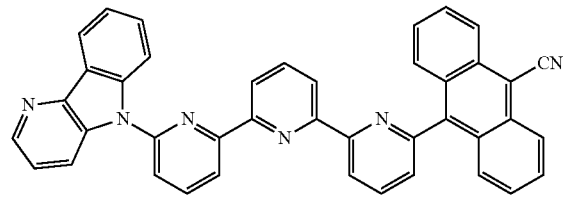
[Chem. 196]
(Compound 196)
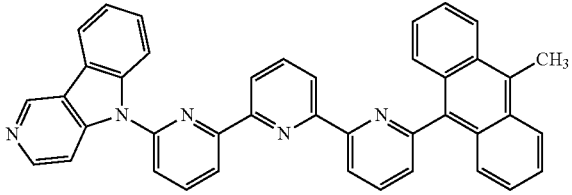
[Chem. 197]
(Compound 197)
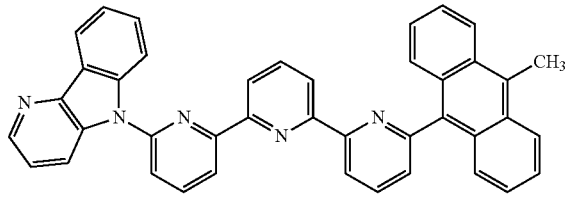
[Chem. 198]
(Compound 198)
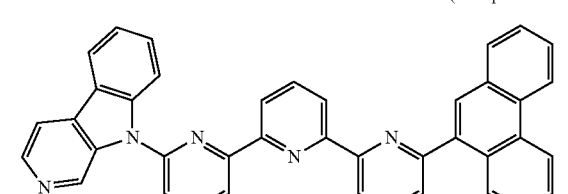
[Chem. 199]
(Compound 199)
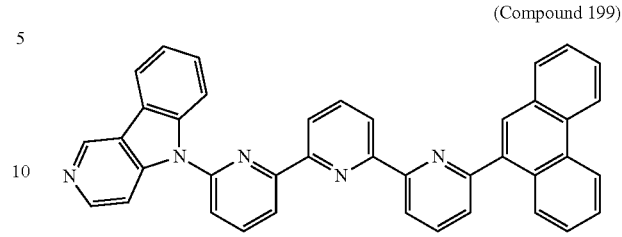
[Chem. 200]
(Compound 200)
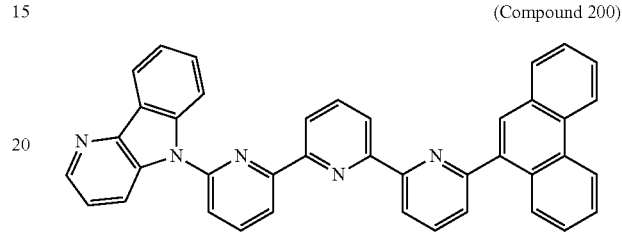
[Chem. 201]
(Compound 201)
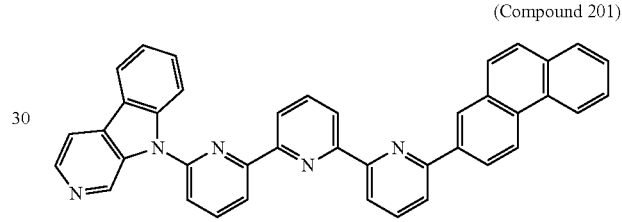
[Chem. 202]
(Compound 202)
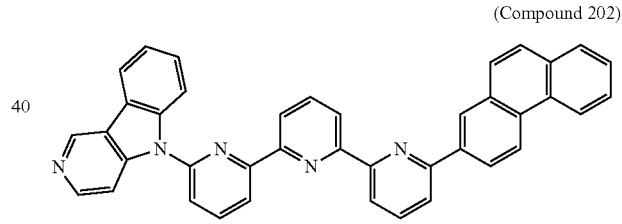
[Chem. 203]
(Compound 203)
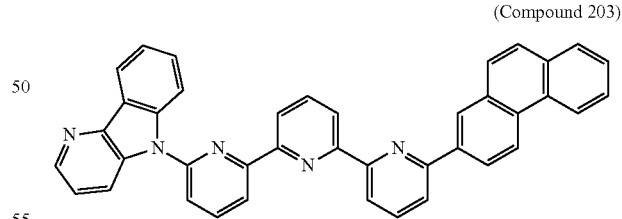
[Chem. 204]
(Compound 204)
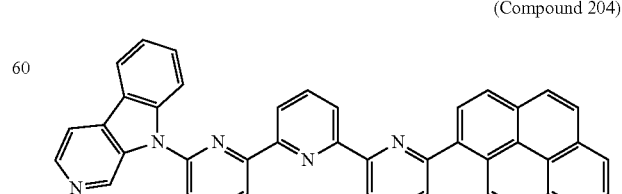

[Chem. 205]
(Compound 205)
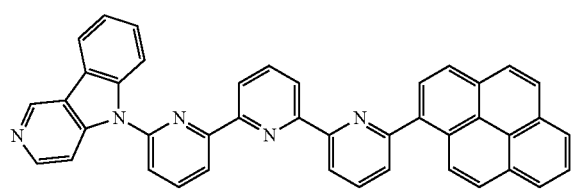
[Chem. 206]
(Compound 206)
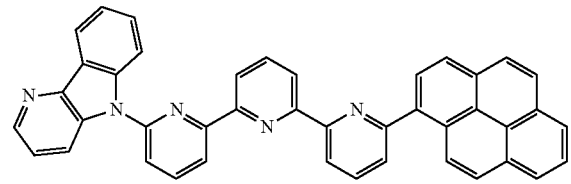
[Chem. 207]
(Compound 207)
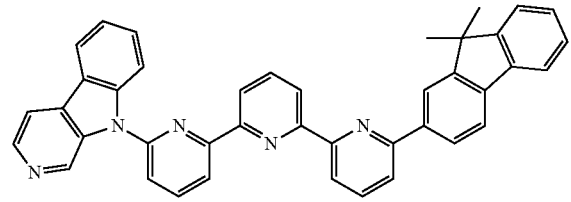
[Chem. 208]
(Compound 208)
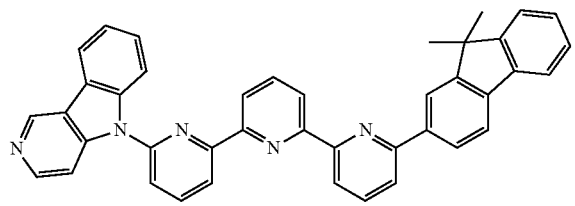
[Chem. 209]
(Compound 209)
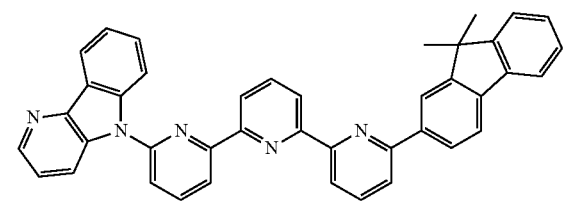
[Chem. 210]
(Compound 210)
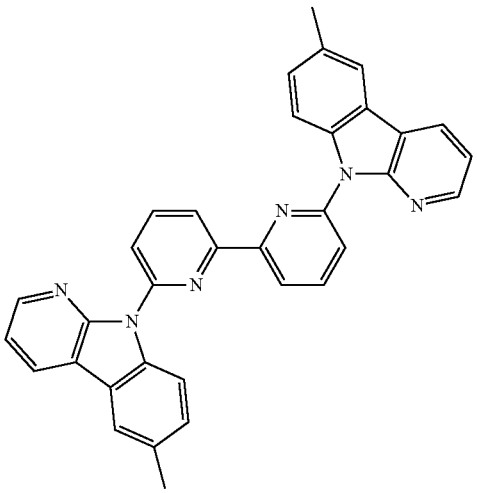
[Chem. 211]
(Compound 211)
[Chem. 212]
(Compound 212)
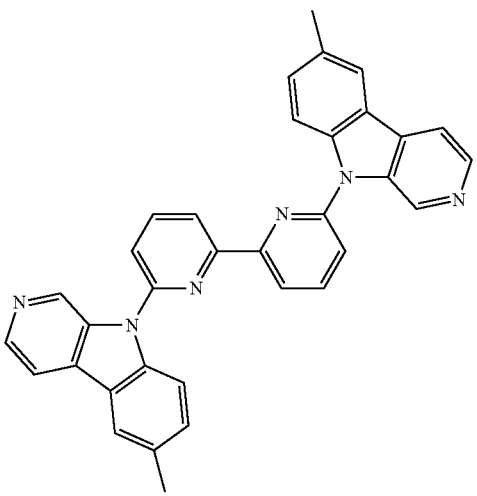

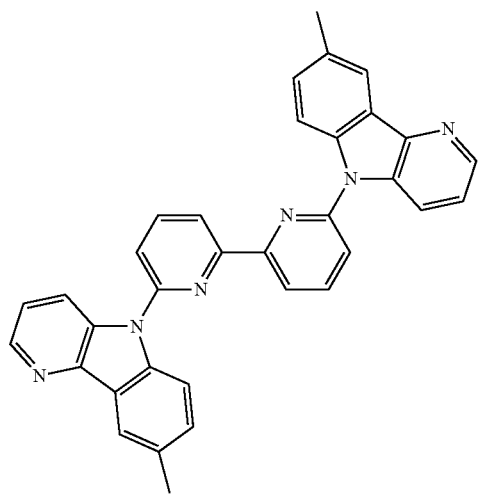
Purification of these compounds was performed by purification by column chromatography, adsorption purification with silica gel, alumina, activated clay or active carbon, a recrystallization or crystallization method with a solvent, or the like. Identification of the compounds can be performed by NMR analysis. As physical properties, DSC measurement (Tg) and measurement of melting point were performed. The melting point serves as an index of vapor deposition properties and the glass transition point (Tg) serves as an index of stability in a thin-film state.

The melting point and the glass transition point were measured using a powder material by means of a highly sensitive differential scanning calorimeter DSC 3100S manufactured by Bruker AXS.

Further, the work function was measured by preparing a thin film of 100 nm on an ITO substrate and using an atmospheric photoelectric spectrometer AC3 type manufactured by Riken Keiki Co., Ltd. The work function is regarded as an indicator of hole-blocking ability.

Examples of the structure of the organic EL device of the invention include a structure having an anode, a hole-injecting layer, a hole-transporting layer, an emitting layer, a hole-blocking layer, an electron-transporting layer and a cathode in this order on a substrate, and a structure further having an electron-injecting layer between the electron-transporting layer and the cathode. In these multilayer structures, it is possible to omit several layers of the organic layers and, for example, the structure may have a constitution sequentially having an anode, a hole-transporting layer, an emitting layer, an electron-transporting layer and a cathode on a substrate.

As the anode of the organic EL device, an electrode material having a large work function, such as ITO or gold, is used. As the hole-injecting layer, besides copper phthalocyanine (hereinafter referred to as CuPc), materials such as star-burst type triphenylamine derivatives and wet-process type materials may be employed.

For the hole-transporting layer, N,N'-diphenyl-N,N'-di(m-tolyl)-benzidine (hereinafter referred to as TPD) and N,N'-diphenyl-N,N'-di(α-naphthyl)-benzidine (hereinafter referred to as NPD), various triphenylamine tetramers, or the like may be used. Further, as the hole-injecting/transporting layers, wet-process type polymer materials such as PEDOT/PSS may be employed.

As the emitting layer, hole-blocking layer, and electron-transporting layer of the organic EL device of the invention, besides the compound having a pyridoindole ring structure having a substituted pyridyl group attached thereto represented by the general formula (1), aluminum complexes, thiazole derivatives, oxazole derivatives, carbazole derivatives, polydialkylfluorene derivatives, or the like may be used.

By using a conventional luminescence material such as an aluminum complex or styryl derivative for the emitting layer and using the compound having a pyridoindole ring structure having a substituted pyridyl group attached thereto represented by the general formula (1) as the hole-blocking layer and the electron-transporting layer, a high-performance organic EL device can be prepared. Further, a high-performance organic EL device can be prepared also by adding a dopant, for example, a fluorescent material such as quinacridone, coumarin or rubrene or a phosphorescent material such as an iridium complex of phenylpyridine, as a host material of the emitting layer.

Furthermore, the compound having a pyridoindole ring structure having a substituted pyridyl group attached thereto, which is represented by the general formula (1), can be used as the electron-transporting layer through multilayering or co-deposition with conventional electron-transporting material(s).

The organic EL device of the invention may have an electron-injecting layer. As the electron-injecting layer, lithium fluoride or the like may be used. For the cathode, an electrode material having a low work function such as aluminum, or an alloy having a low work function such as aluminum magnesium is used as an electrode material.

Embodiments of the present invention will be illustrated in greater detail with reference to the following Examples, but the invention should not be construed as being limited thereto so long as not exceeding the gist thereof.

Example 1

Synthesis of 9,9'-[6,6'-bipyridine]-2,2'-diyl-bis-9H-pyrido[2,3-b]indol (Compound 2)

2.0 g of 6,6'-Dibromo-2,2'-bipyridine, 2.4 g of 9H-pyrido[2,3-b]indol, 0.2 g of copper powder, 2.6 g of potassium carbonate, 0.2 ml of dimethyl sulfoxide, and 24 ml of o-dichlorobenzene were added and the whole was stirred for 30 hours under heating and refluxing. After cooling to room temperature, 100 ml of toluene was added thereto and insoluble solid was removed by filtration. After 200 ml of water was added to the insoluble solid and then stirring and washing was performed, 350 ml of o-dichlorobenzene was added and the whole was stirred under heating to 150° C. to effect washing. The resulting crude product was washed with methanol and then dried under reduced pressure at 70° C. for 12 hours to obtain 2.40 g (yield 77%) of 9,9'-[6,6'-bipyridine]-2,2'-diyl-bis-9H-pyrido[2,3-b]indol (Compound 2) as a white powder.

The structure of the resulting white powder was identified using NMR. The results of 1H-NMR measurement are shown in FIG. 1.

The following 20 hydrogen signals were detected on 1H-NMR(CF3COOD). δ (ppm)=9.69 (2H), 9.16 (2H), 9.07 (2H), 8.95-9.00 (4H), 8.76 (2H), 8.54 (2H), 8.27-46 (6H).

Example 2

Synthesis of 5,5'-[6,6'-bipyridine]-2,2'-diyl-bis-5H-pyrido[4,3-b]indol (Compound 4)

2.0 g of 6,6'-Dibromo-2,2'-bipyridine, 2.4 g of 5H-pyrido[4,3-b]indol, 0.2 g of copper powder, 2.6 g of potassium carbonate, 0.2 ml of dimethyl sulfoxide, and 24 ml of o-dichlorobenzene were added and the whole was stirred for 15 hours under heating and refluxing. After cooling to room temperature, 200 ml of chloroform was added thereto and insoluble solid was removed by filtration. After 300 ml of a mixed solution of chloroform/methanol=4/1 (v/v) was added to the insoluble solid to dissolve it, insoluble solid was removed by filtration. After the filtrate was washed with 300 ml of water and dried over magnesium sulfate, the filtrate was concentrated under reduced pressure to obtain a crude product. The crude product was purified by column chromatography (carrier: NH silica gel, eluent: chloroform) to obtain 1.25 g (yield 40%) of 5,5'-[6,6'-bipyridine]-2,2'-diyl-bis-5H-pyrido[4,3-b]indol (Compound 4) as a white powder.

Figure 2:
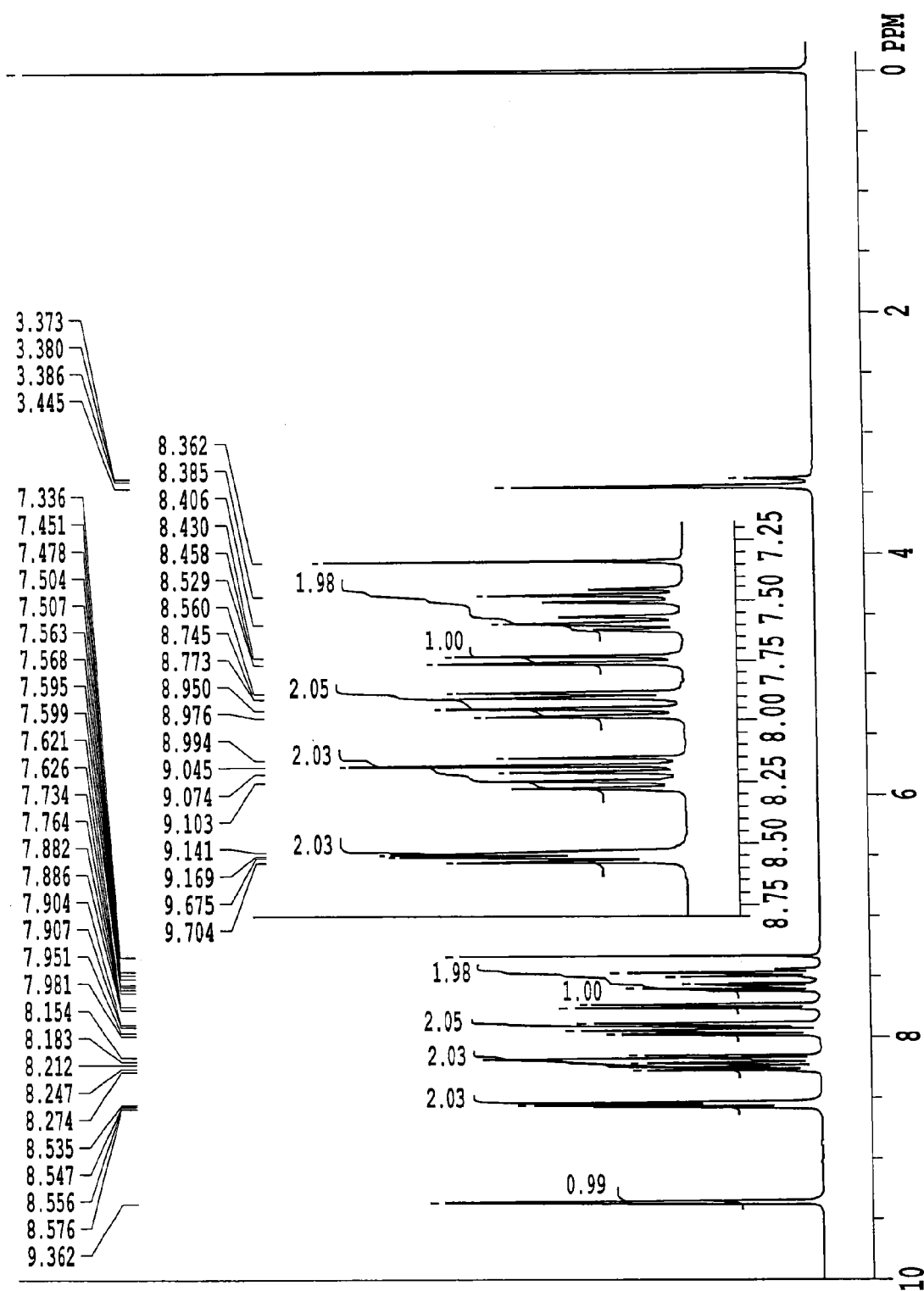
FIG. 2 is a 1H-NMR chart of the compound (Compound 4) of Invention Example 2.

The structure of the resulting white powder was identified using NMR. The results of $^1$H-NMR measurement are shown in FIG. 2.

The following 20 hydrogen signals were detected on 1H-NMR (CDCl3-CD3OD). δ (ppm)=9.36 (2H), 8.50-58 (4H), 8.26 (2H), 8.18 (2H), 7.97 (2H), 7.89 (2H), 7.75 (2H), 7.62 (6H), 7.48 (2H).

Example 3

Synthesis of 9,9'-[2,2';6',2"-terpyridine]-6,6"-diyl-bis-9H-pyrido[2,3-b]indol (Compound 6)

1.0 g of 6,6"-Dibromo-2,2'; 6',2"-terpyridine, 0.95 g of 9H-pyrido[2,3-b]indol, 82 mg of copper powder, 1.1 g of potassium carbonate, 0.08 ml of dimethyl sulfoxide, and 10 ml of o-dichlorobenzene were added and the whole was stirred for 16 hours under heating and refluxing. After cooling to room temperature, 50 ml of toluene was added thereto and insoluble solid was removed by filtration. After 200 ml of a mixed solution of chloroform/methanol=5/1 (v/v) was added to the insoluble solid to dissolve it, insoluble solid was removed by filtration. After the filtrate was washed with 300 ml of water and dried over magnesium sulfate, the filtrate was concentrated under reduced pressure to obtain a crude product. The crude product was purified by recrystallization from o-dichlorobenzene and then the purified product was dried under reduced pressure at 70° C. for 12 hours to obtain 960 mg (yield 66%) of 9,9'-[2,2'; 6',2"-terpyridine]-6,6"-diyl-bis-9H-pyrido[2,3-b]indol (Compound 6) as a white powder.

Figure 3:
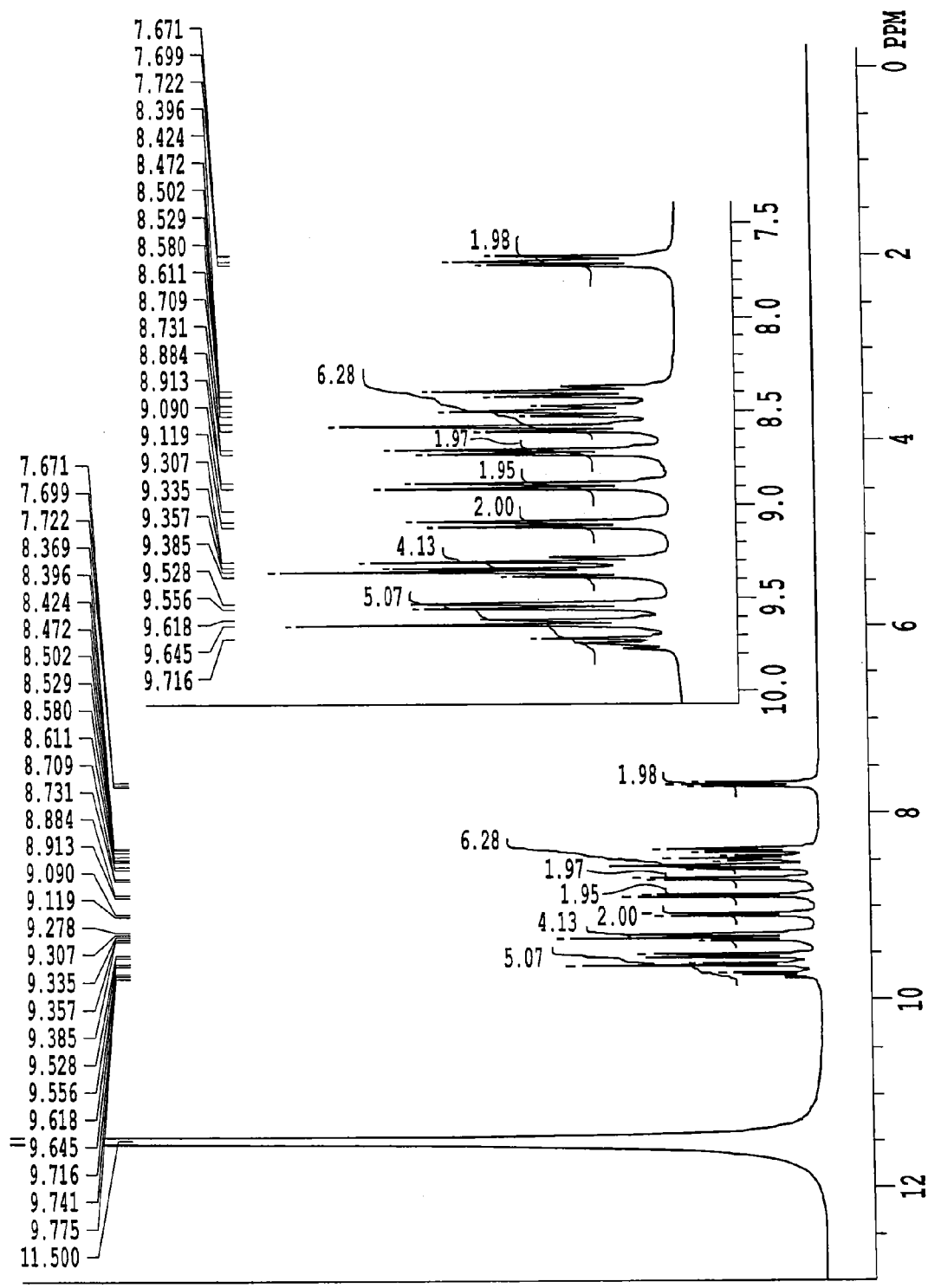
FIG. 3 is a 1H-NMR chart of the compound (Compound 6) of Invention Example 3.

The structure of the resulting white powder was identified using NMR. The results of 1H-NMR measurement are shown in FIG. 3.

The following 23 hydrogen signals were detected on 1H-NMR(CF3COOD). δ (ppm)=9.72-78 (1H), 9.63 (2H), 9.54 (2H), 9.28-39 (4H), 9.10 (2H), 8.90 (2H), 8.72 (2H), 8.60 (2H), 8.50 (2H), 8.40 (2H), 7.70 (2H).

Example 4

Synthesis of 5,5'-[2,2'; 6',2"-terpyridine]-6,6"-diyl-bis-5H-pyrido[4,3-b]indol (Compound 9)

1.0 g of 6,6"-Dibromo-2,2'; 6',2"-terpyridine, 0.95 g of 5H-pyrido[4,3-b]indol, 82 mg of copper powder, 1.1 g of potassium carbonate, 0.08 ml of dimethyl sulfoxide, and 10 ml of o-dichlorobenzene were added and the whole was stirred for 10 hours under heating and refluxing. After cooling to room temperature, 50 ml of toluene was added thereto and insoluble solid was removed by filtration. After 300 ml of a mixed solution of chloroform/methanol=4/1 (v/v) was added to the insoluble solid to dissolve it, insoluble solid was removed by filtration. After the filtrate was washed with 300 ml of water and dried over magnesium sulfate, the filtrate was concentrated under reduced pressure to obtain a crude product. The crude product was purified by column chromatography (carrier: NH silica gel, eluent: chloroform/methanol) to obtain 893 mg (yield 62%) of 5,5'-[2,2'; 6',2"-terpyridine]-6,6"-diyl-bis-5H-pyrido[4,3-b]indol (Compound 9) as a white powder.

Figure 4:
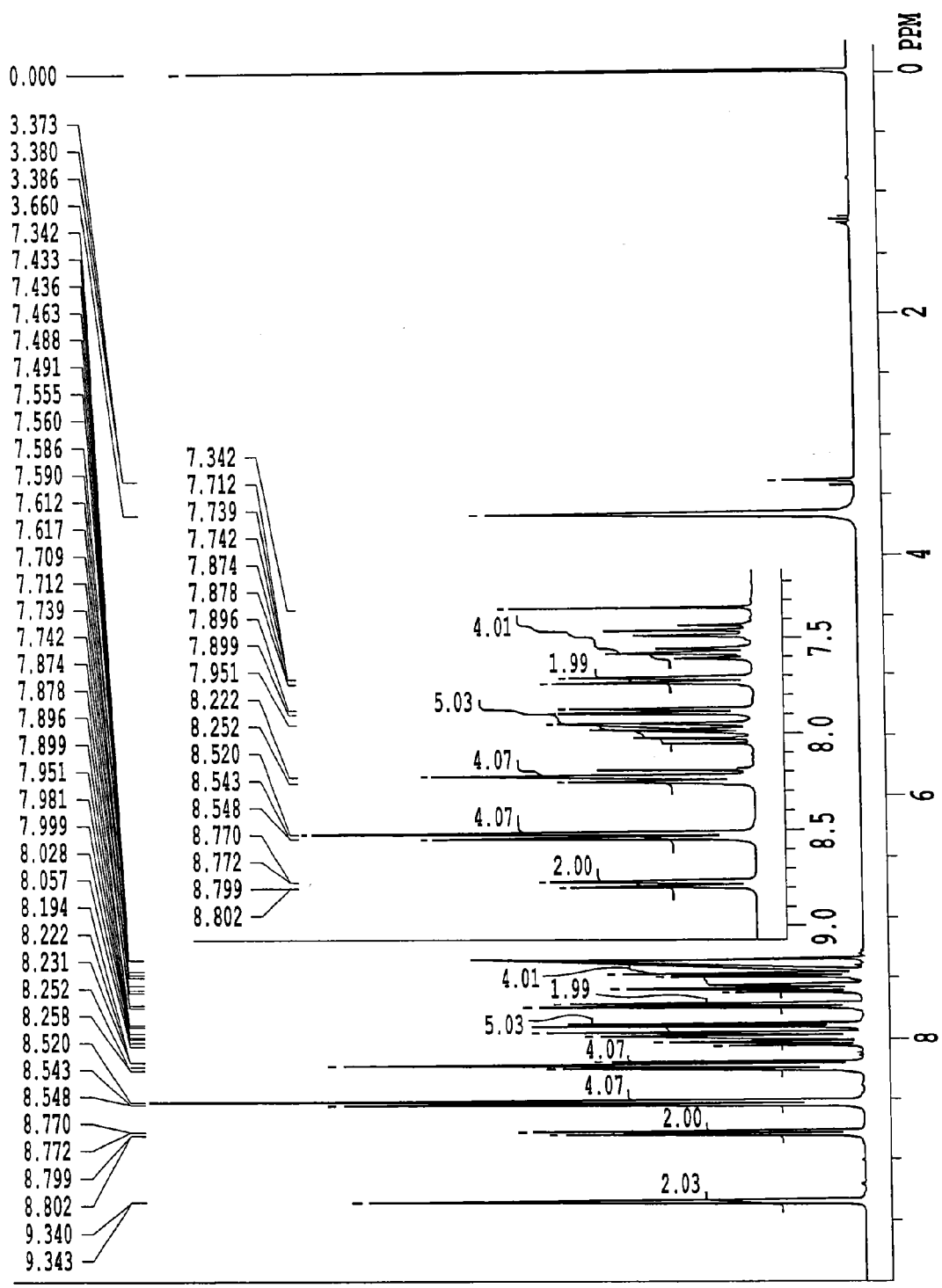
FIG. 4 is a 1H-NMR chart of the compound (Compound 9) of Invention Example 4.

The structure of the resulting white powder was identified using NMR. The results of 1H-NMR measurement are shown in FIG. 4.

The following 23 hydrogen signals were detected on 1H-NMR (CDCl3-CD3OD). δ (ppm)=9.34 (2H), 8.78 (2H), 8.53 (4H), 8.19-26 (4H), 7.87-8.06 (5H), 7.73 (2H), 7.59 (2H), 7.46 (2H).

Example 5

Synthesis of 5,5'-[2,2'; 6',2"-terpyridine]-6,6"-diyl-bis-5H-pyrido[3,2-b]indol (Compound 10)

1.2 g of 6,6"-Dibromo-2,2'; 6',2"-terpyridine, 1.1 g of 5H-pyrido[3,2-b]indol, 95 mg of copper powder, 1.2 g of potassium carbonate, 0.09 ml of dimethyl sulfoxide, and 10 ml of o-dichlorobenzene were added and the whole was stirred for 6 hours under heating and refluxing. After cooling to room temperature, 50 ml of toluene was added thereto and insoluble solid was removed by filtration. After 300 ml of a mixed solution of chloroform/methanol=4/1 (v/v) was added to the insoluble solid to dissolve it, insoluble solid was removed by filtration. After the filtrate was washed with 300 ml of water and dried over magnesium sulfate, the filtrate was concentrated under reduced pressure to obtain a crude product. The crude product was purified by column chromatography (carrier: NH silica gel, eluent: chloroform/methanol) to obtain 761 mg (yield 45%) of 5,5'-[2,2'; 6',2"-terpyridine]-6,6"-diyl-bis-5H-pyrido[3,2-b]indol (Compound 10) as a white powder.

Figure 5:
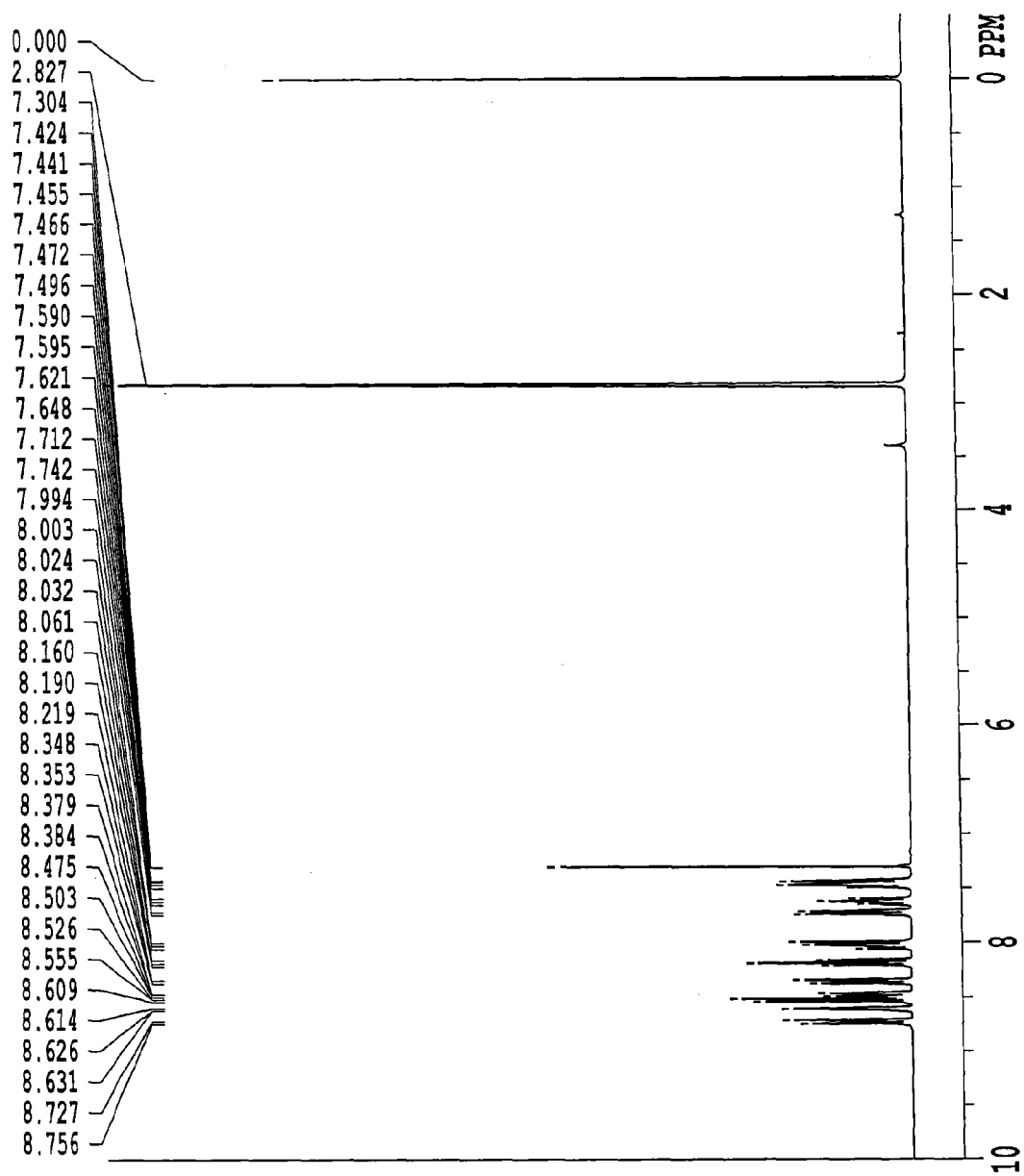
FIG. 5 is a 1H-NMR chart of the compound (Compound 10) of Invention Example 5.

The structure of the resulting white powder was identified using NMR. The results of 1H-NMR measurement are shown in FIG. 5.

The following 23 hydrogen signals were detected on 1H-NMR (CDCl3-CD3OD). δ (ppm)=8.74 (2H), 8.62 (2H), 8.54 (2H), 8.49 (2H), 8.37 (2H), 8.19 (2H), 7.99-8.06 (3H), 7.73 (2H), 7.62 (2H), 7.42-50 (4H).

Example 6

Synthesis of 6'-(10-phenylanthracen-9-yl)-6-(5H-pyrido[4,3-b]indol-5-yl)-[2,2']bipyridine (Compound 67)

1.2 g of 6'-bromo-6-5H-pyrido[4,3-b]indol-5-yl-[2,2']bipyridine, 1.4 g of 9-(4,4,5,5-tetramethyl-[1,3,2]dioxaborolan-2-yl)-10-phenylanthracene, 15 ml of a 2M potassium carbonate aqueous solution, 180 mg of tetrakis(triphenylphosphine)palladium(0), 120 ml of toluene, and 30 ml of ethanol were added and the whole was stirred for 28 hours under heating and refluxing. After cooling to room temperature and concentration was performed under reduced pressure, 200 ml of chloroform was added thereto to effect dissolution. After the solution was washed with 100 ml of a saturated sodium chloride solution and dried over magnesium sulfate, the solution was concentrated under reduced pressure to obtain a crude product. The crude product was purified by column chromatography (carrier: NH silica gel, eluent: chloroform/hexane) to obtain 1.67 g (yield 97%) of 6'-(10-phenylanthracen-9-yl)-6-(5H-pyrido[4,3-b]indol-5-yl)-[2,2']bipyridine (Compound 67) as a white powder.

Figure 6:
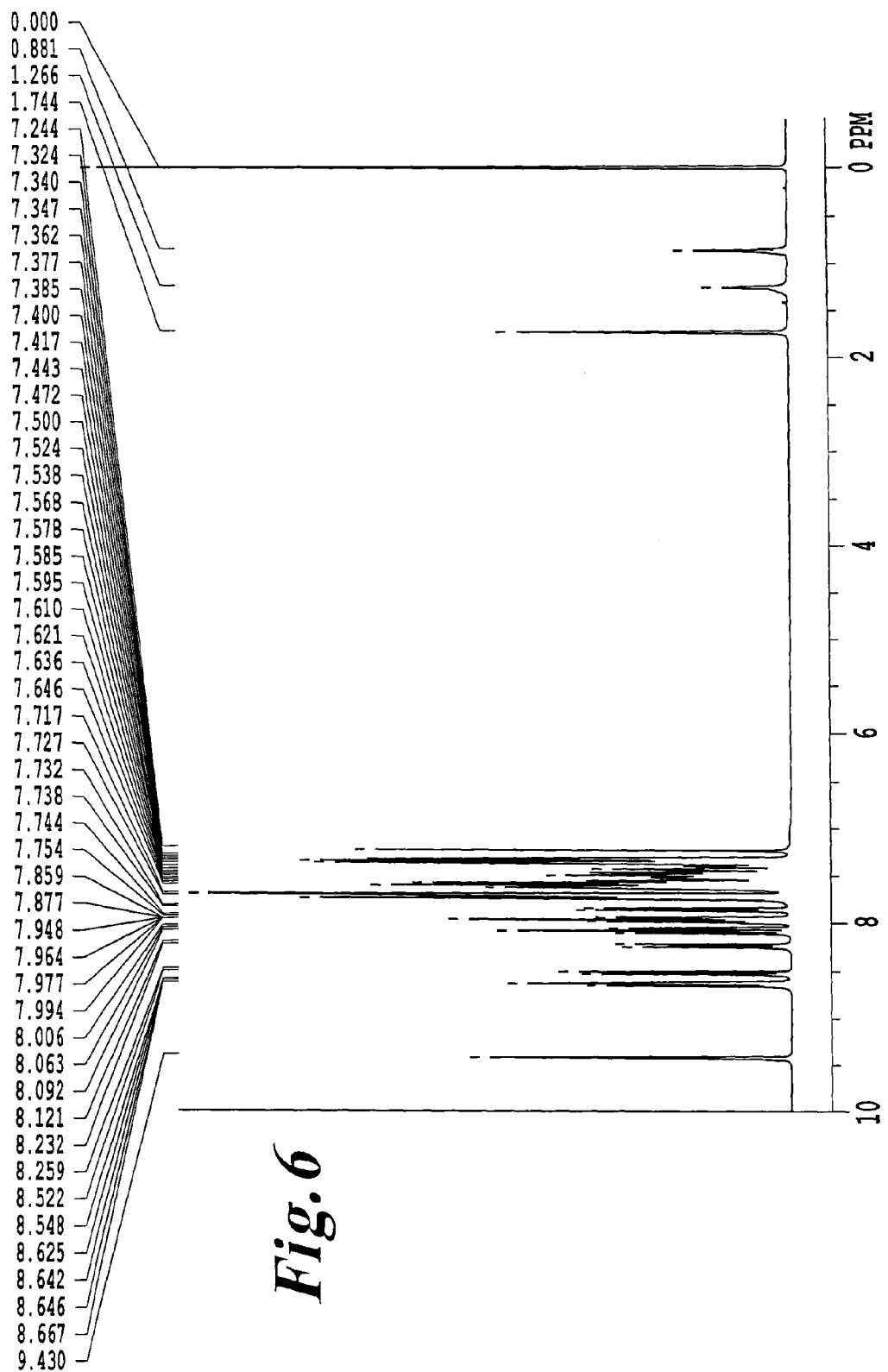
FIG. 6 is a 1H-NMR chart of the compound (Compound 67) of Invention Example 6.

The structure of the resulting white powder was identified using NMR. The results of 1H-NMR measurement are shown in FIG. 6.

The following 26 hydrogen signals were detected on 1H-NMR (CDCl3). δ (ppm)=9.43 (1H), 8.63-67 (2H), 8.53 (1H), 8.25 (1H), 8.09 (1H), 7.95-8.01 (2H), 7.87 (1H), 7.72-75 (4H), 7.32-65 (13H).

Example 7

Synthesis of 1,3-bis[5H-pyrido[4,3-b]indol-5-yl-pyridine-6-yl]benzene (Compound 124)

3.5 g of 5-(6-bromopyridin-2-yl)-5H-pyrido[4,3-b]indol, 0.9 g of benzene-1,3-diboronic acid, 27 ml of a 2M potassium carbonate aqueous solution, 185 mg of tetrakis(triphenylphosphine)palladium(0), 300 ml of toluene, and 75 ml of ethanol were added and the whole was stirred for 7 hours under heating and refluxing. After cooling to room temperature, 400 ml of water was added thereto and extraction with 200 ml of toluene was performed. After the extract was dried over magnesium sulfate, the extract was concentrated under reduced pressure to obtain a crude product. The crude product was purified by column chromatography (carrier: NH silica gel, eluent: chloroform/hexane) to obtain 1.62 g (yield 54%) of 1,3-bis[5H-pyrido[4,3-b]indol-5-yl-pyridine-6-yl]benzene (Compound 124) as a white powder.

Figure 7:
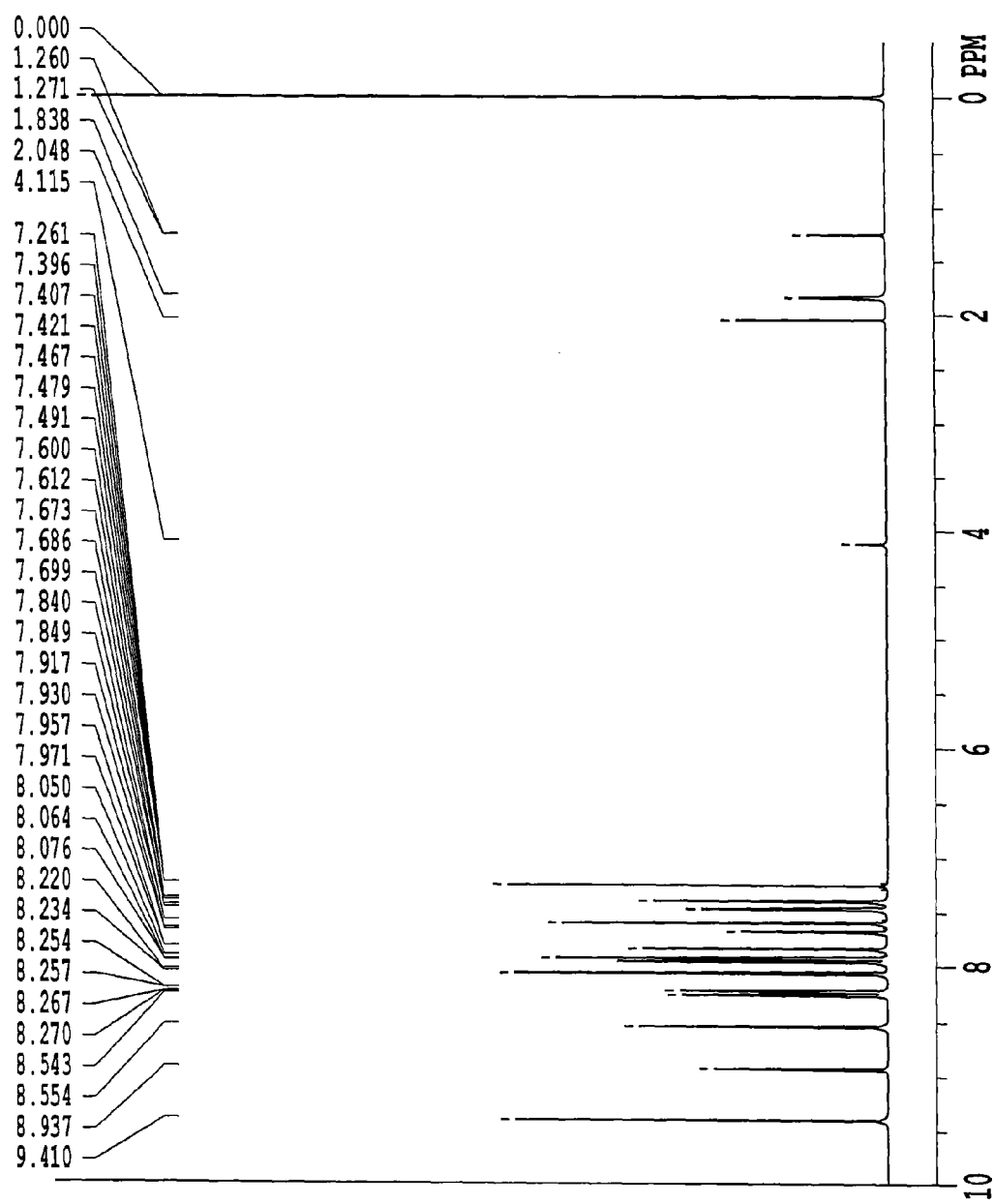
FIG. 7 is a 1H-NMR chart of the compound (Compound 124) of Invention Example 7.

The structure of the resulting white powder was identified using NMR. The results of 1H-NMR measurement are shown in FIG. 7.

The following 24 hydrogen signals were detected on 1H-NMR (CDCl3). δ (ppm)=9.41 (2H), 8.94 (1H), 8.55 (2H), 8.27 (2H), 8.23 (2H), 8.06 (2H), 7.97 (2H), 7.93 (2H), 7.85 (2H), 7.69 (1H), 7.61 (2H), 7.48 (2H), 7.41 (2H).

Example 8

Synthesis of 1,4-bis[5H-pyrido[4,3-b]indol-5-yl-pyridine-6-yl]benzene (Compound 129)

1.5 g of 5-(6-bromopyridin-2-yl)-5H-pyrido[4,3-b]indol, 0.4 g of benzene-1,4-diboronic acid, 11 ml of a 2M potassium carbonate aqueous solution, 74 mg of tetrakis(triphenylphosphine)palladium(0), 120 ml of toluene, and 30 ml of ethanol were added and the whole was stirred for 3 hours under heating and refluxing. After cooling to room temperature, insoluble solid was removed by filtration. The resulting solid was dissolved in a mixed solution of chloroform/methanol and insoluble solid was removed by filtration. Thereafter, the filtrate was concentrated under reduced pressure to obtain a crude product. The crude product was purified by recrystallization from methanol to obtain 0.91 g (yield 76%) of 1,4-bis[5H-pyrido[4,3-b]indol-5-yl-pyridine-6-yl]benzene (Compound 129) as a yellow white powder.

Figure 8:
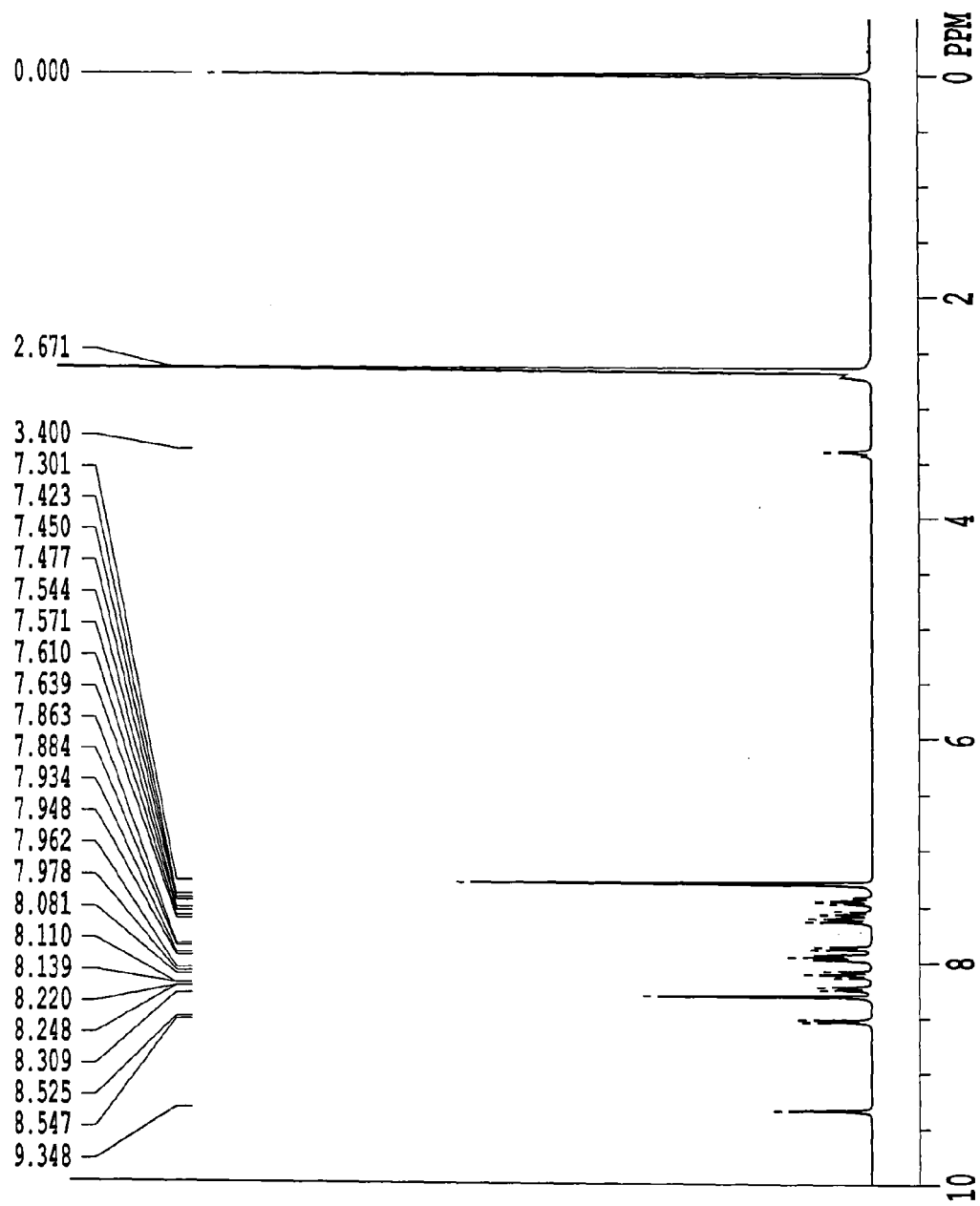
FIG. 8 is a 1H-NMR chart of the compound (Compound 129) of Invention Example 8.

The structure of the resulting yellow white powder was identified using NMR. The results of 1H-NMR measurement are shown in FIG. 8.

The following 24 hydrogen signals were detected on 1H-NMR (CDCl3-CD3OD). δ (ppm)=9.35 (2H), 8.54 (2H), 8.31 (4H), 8.23 (2H), 8.11 (2H), 7.93-98 (4H), 7.87 (2), 7.54-64 (4H), 7.45 (2H).

Example 9

Synthesis of 6'-(4-benzothiazol-2-yl-phenyl)-6-(5H-pyrido[4,3-b]indol-5-yl)-[2,2']bipyridine (Compound 155)

1.1 g of 6'-Bromo-6-5H-pyrido[4,3-b]indol-5-yl-[2,2']bipyridine, 0.9 g of 2-[4-(4,4,5,5-tetramethyl-[1,3,2]dioxaborolan-2-yl)phenyl]benzothiazole, 13 ml of a 2M potassium carbonate aqueous solution, 150 mg of tetrakis (triphenylphosphine)palladium(0), 120 ml of toluene, and 30 ml of ethanol were added and the whole was stirred for 4 hours under heating and refluxing. After cooling to room temperature and concentration was performed under reduced pressure, 200 ml of chloroform was added thereto to effect dissolution. After the solution was washed with 100 ml of a saturated sodium chloride solution and dried over magnesium sulfate, the solution was concentrated under reduced pressure to obtain a crude product. The crude product was purified by column chromatography (carrier: NH silica gel, eluent: chloroform/hexane) to obtain 0.84 g (yield 63%) of 6'-(4-benzothiazol-2-yl-phenyl)-6-(5H-pyrido[4,3-b]indol-5-yl)-[2,2']bipyridine (Compound 155) as a white powder.

Figure 9:
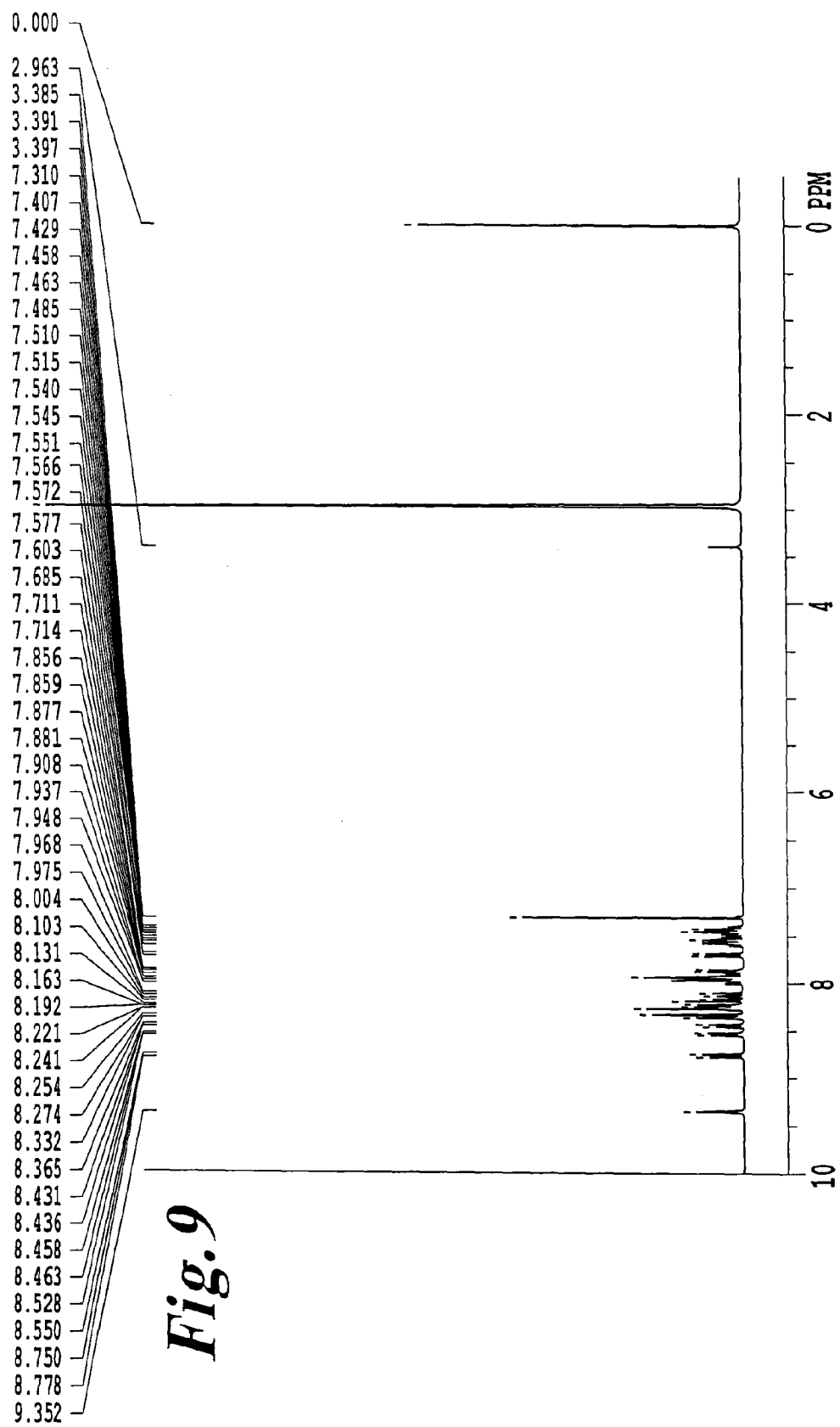
FIG. 9 is a 1H-NMR chart of the compound (Compound 155) of Invention Example 9.

The structure of the resulting white powder was identified using NMR. The results of 1H-NMR measurement are shown in FIG. 9.

The following 21 hydrogen signals were detected on 1H-NMR (CDCl3-CD3OD). δ (ppm)=9.35 (1H), 8.76 (1H), 8.54 (1H), 8.45 (1H), 8.10-37 (7H), 7.86-8.00 (5H), 7.70 (1H), 7.41-60 (4H).

Example 10

Synthesis of 6''-naphthalen-1-yl-6-5H-pyrido[4,3-b]indol-5-yl-[2,2';6',2'']terpyridine (Compound 164)

0.9 g of 6''-Bromo-6-5H-pyrido[4,3-b]indol-5-yl-[2,2';6',2'']terpyridine, 0.39 g of naphthaleneboronic acid, 9 ml of a 2M potassium carbonate aqueous solution, 0.1 g of tetrakis (triphenylphosphine)palladium(0), 120 ml of toluene, and 30 ml of ethanol were added and the whole was stirred for 6 hours under heating and refluxing. After cooling to room temperature, 200 ml of water was added thereto and extraction with 150 ml of chloroform was performed. After dried over magnesium sulfate, the extract was concentrated under reduced pressure to obtain a crude product. The crude product was purified by column chromatography (carrier: NH silica gel, eluent: chloroform) to obtain 799 mg (yield 80%) of 6''-naphthalen-1-yl-6-5H-pyrido[4,3-b]indol-5-yl-[2,2';6',2'']terpyridine (Compound 164) as a white powder.

Figure 10:
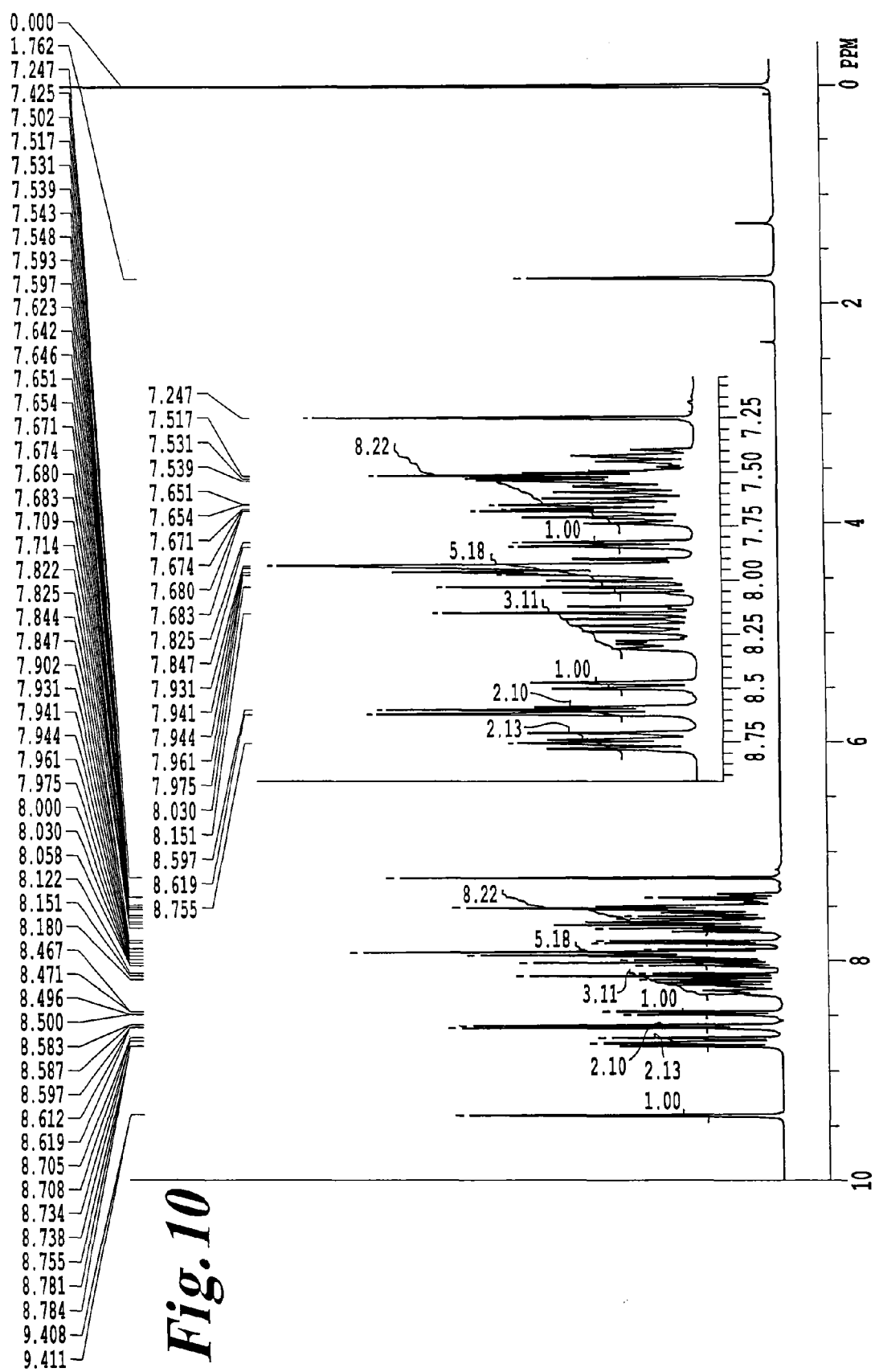
FIG. 10 is a 1H-NMR chart of the compound (Compound 164) of Invention Example 10.

The structure of the resulting white powder was identified using NMR. The results of 1H-NMR measurement are shown in FIG. 10.

The following 23 hydrogen signals were detected on 1H-NMR (CDCl3). δ (ppm)=9.41 (1H), 8.71-78 (2H), 8.58-62 (2H), 8.47-50 (1H), 8.10-31 (3H), 7.90-8.06 (5H), 7.84 (1H), 7.43-72 (8H).

Example 11

For the compounds of the invention, melting point and glass transition point were determined by means of a highly sensitive differential scanning calorimeter (DSC 3100S manufactured by Bruker AXS). In this connection, "-" shown in the following results of the glass transition point means that glass transition point was not observed.

|  | Melting Point | Glass Transition Point |
| --- | --- | --- |
| Compound of invention Example 1 | 359° C. | — |
| Compound of invention Example 2 | 375° C. | — |
| Compound of invention Example 3 | 324° C. | — |
| Compound of invention Example 4 | 307° C. | 129° C. |
| Compound of invention Example 5 | 291° C. | 126° C. |
| Compound of invention Example 6 | 291° C. | 141° C. |
| Compound of invention Example 7 | 287° C. | 123° C. |
| Compound of invention Example 8 | 376° C. | — |
| Compound of invention Example 9 | 258° C. | 99° C. |
| Compound of invention Example 10 | 207° C. | 98° C. |

The compounds of the invention show a glass transition point of 90° C. or higher or show no glass transition point, and thus are stable in a thin-film state.

Example 12

Using each of the compounds of the invention, a deposited film having a film thickness of 100 nm was prepared on an ITO substrate and work function was measured on an atmospheric photoelectron spectrometer (AC3 type, manufactured by Riken Keiki Co., Ltd.).

|   | Work Function |
|---|---|
| Compound of invention Example 1 | 5.7 eV |
| Compound of invention Example 2 | 6.1 eV |
| Compound of invention Example 4 | 5.9 eV |
| Compound of invention Example 5 | 6.3 eV |
| Compound of invention Example 6 | 6.5 eV |
| Compound of invention Example 7 | 6.3 eV |
| Compound of invention Example 8 | 6.1 eV |

Thus, the compounds of the invention have values deeper than a work function of 5.4 eV possessed by common hole-transporting materials such as NPD and TPD and have a large hole-blocking ability.

Example 13

A thermal resistance test was performed at 300° C. for 1 week. The thermal resistance test was performed as follows. A sample (10 mg) was placed in a glass test tube and, after evacuation to vacuum by means of a diaphragm pump, the test tube was sealed. The sealed tube containing the sample was placed in a constant-temperature chamber set at a predetermined temperature and allowed to stand. After the passage of a predetermined period, the evacuated sealed tube was broken and HPLC purity of the sample was measured. The HPLC purity was measured under the following measuring conditions. Column: Inertsil ODS-SP (inner diameter 4.6 mm, length 250 mm), Mobile phase: acetonitrile/0.05% (v/v) trifluoroacetic acid aqueous solution=35/65 (v/v), Flow rate: 1.0 ml/minute, Column temperature: 40° C., Measuring wavelength: 254 nm. The HPLC purity (peak area percent, %) was as follows.

|   | Before test | After 300° C., 1 week |
|---|---|---|
| Compound of invention Example 4 | 99.6% | 99.0% |
| BCP (Illustrative compound 1) | 99.9% | 94.2% |

As compared with BCP, it is obvious that the compound of invention Example 4 (Compound 9) is excellent in thermal resistance.

[Chem. 222]

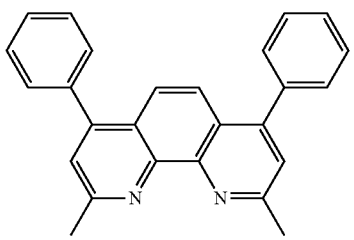

(Illustrative compound 1)

Example 14

Figure 11:
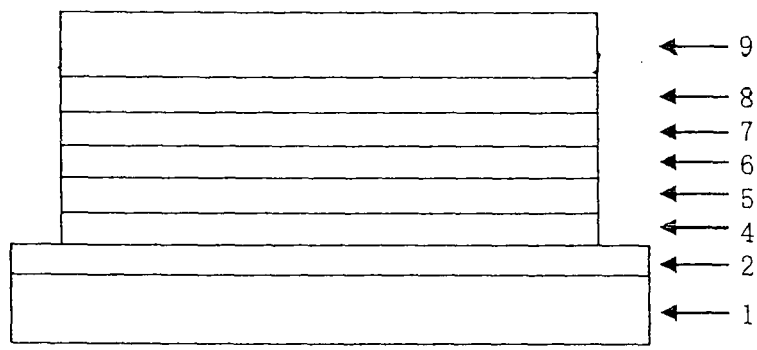
FIG. 11 is a drawing showing the constitution of the EL device of Example 14.
Figure 12:
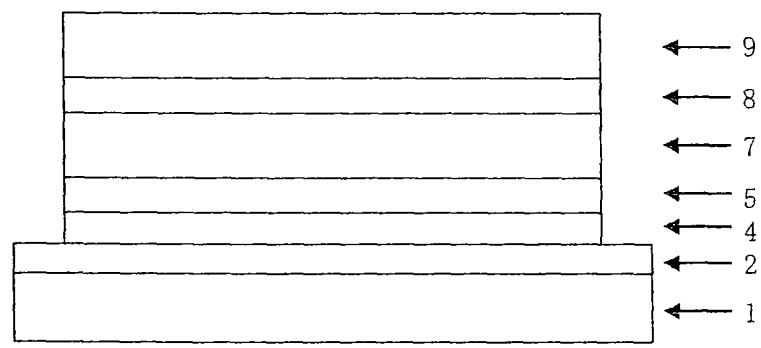
FIG. 12 is a drawing showing the constitution of the EL device of Comparative Example 1.

An organic EL device was prepared by depositing a hole-transporting layer 4, an emitting layer 5, a hole-blocking layer 6, an electron-transporting layer 7, an electron-injecting layer 8, and a cathode (aluminum electrode) 9 in this order on a glass substrate 1 on which an ITO electrode had been formed as a transparent anode 2 in advance, as shown in FIG. 11. After the glass substrate 1 on which ITO having a film thickness of 150 nm had been formed was washed with an organic solvent, the surface was washed by UV ozone treatment. It was mounted in a vacuum deposition machine, which was then evacuated to 0.001 Pa.

Subsequently, NPD was formed thereon at a deposition rate of 6 nm/min to a thickness of about 40 nm as the hole-transporting layer 4. As the emitting layer 5, Alq3 was formed thereon at a deposition rate of 6 nm/min to a thickness of about 20 nm. On the emitting layer 5, the compound of invention Example 4 (Compound 9) was formed at a deposition rate of 6 nm/min to a thickness of about 20 nm as the hole-blocking layer-cum-electron-transporting layer 6 and 7. On the electron-transporting layer 7, lithium fluoride was formed at a deposition rate of 0.6 nm/min to a thickness of about 0.5 nm as the electron-injecting layer 8. Finally, aluminum was deposited to a thickness of about 200 nm to form the cathode 9. The prepared device was stored in a vacuum desiccator and characteristic properties were measured in the atmosphere at ordinary temperature.

The results of applying direct voltage to the organic EL device of the invention thus formed are shown in FIG. 15 to FIG. 18. Namely, a luminescence of 100 cd/m$^2$ was observed from 3.04 V, and at 5.19 V, a current of 300 mA/cm$^2$ flowed to obtain a green luminescence of 7700 cd/m$^2$. The luminous efficiency at the luminance was 2.57 cd/A. Maximum luminance of the device before breakpoint was 24020 cd/m$^2$.

Comparative Example 1

For comparison, an organic EL device was prepared under the same conditions as in Example 14 except that the material of the electron-transporting layer 7 was replaced by Alq3, and characteristic properties thereof were investigated. Namely, Alq3 was formed at a deposition rate of 6 nm/min to a thickness of about 40 nm as the emitting layer-cum-electron-transporting layer 5 and 7. A luminescence of 100 cd/m$^2$ was observed from 3.14 V, and at 5.45 V, a current of 300 mA/cm$^2$ flowed to obtain a green luminescence of 6470 cd/m$^2$. The luminous efficiency at the luminance was 2.16 cd/A. Maximum luminance of the device before breakpoint was 23700 cd/m$^2$. The results are shown in FIG. 15 to FIG. 18 together with the results of Example 14.

Example 15

Figure 13:
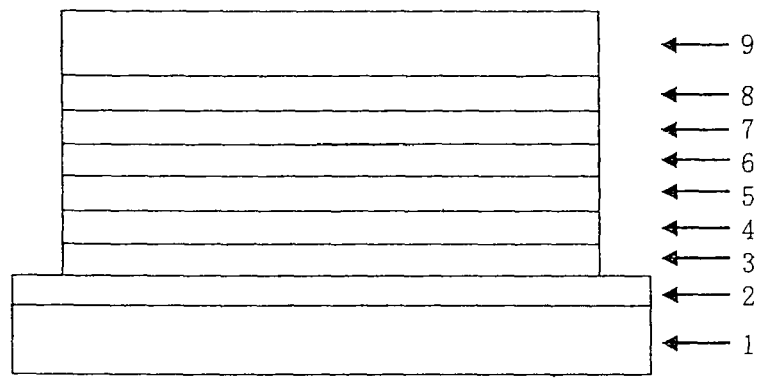
FIG. 13 is a drawing showing the constitution of the EL devices of Examples 15, 16, 17, 18, 19, and 20.
Figure 14:
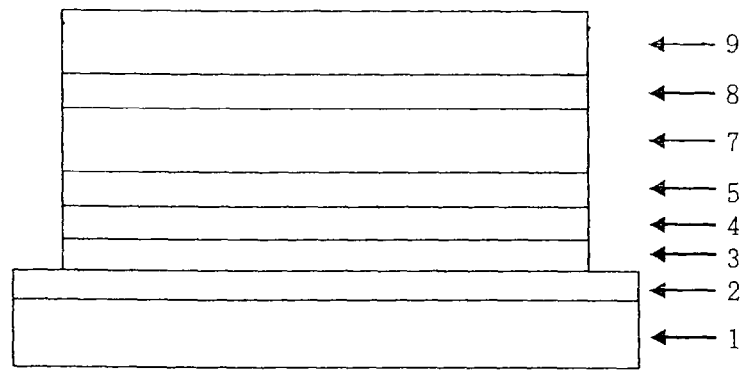
FIG. 14 is a drawing showing the constitution of the EL device of Comparative Example 2.
Figure 15:
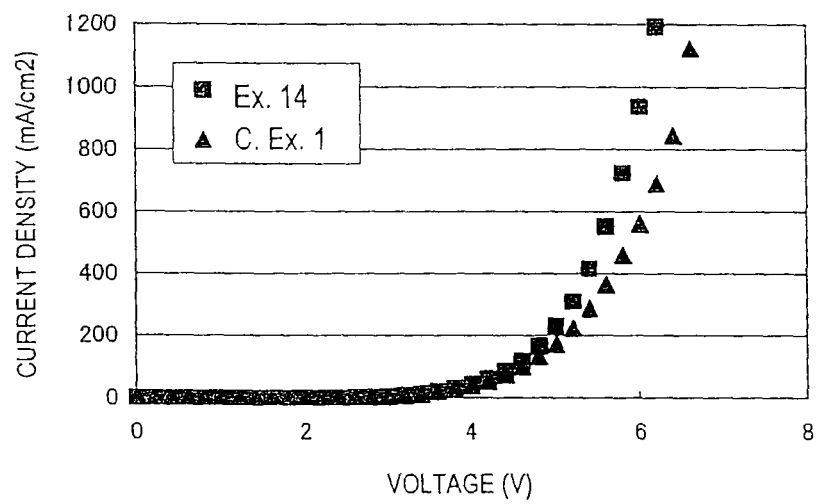
FIG. 15 is a graph comparing voltage/current density properties of Example 14 and Comparative Example 1.
Figure 16:
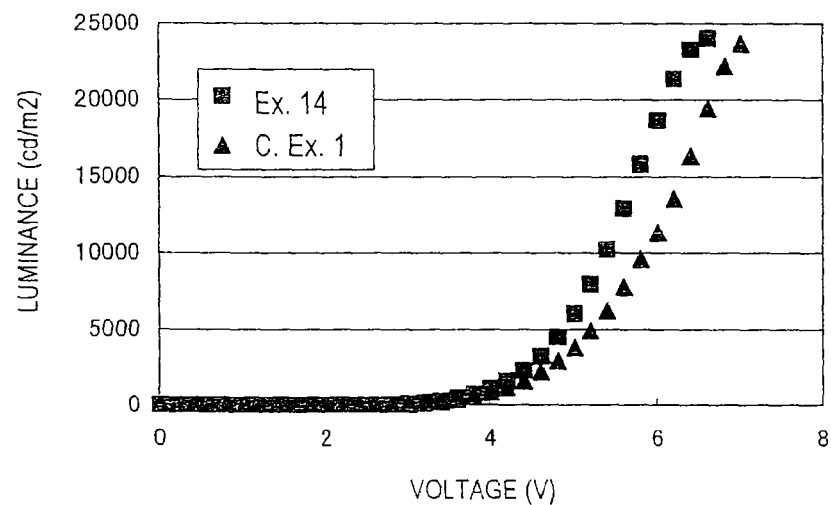
FIG. 16 is a graph comparing voltage/luminance properties of Example 14 and Comparative Example 1.
Figure 17:
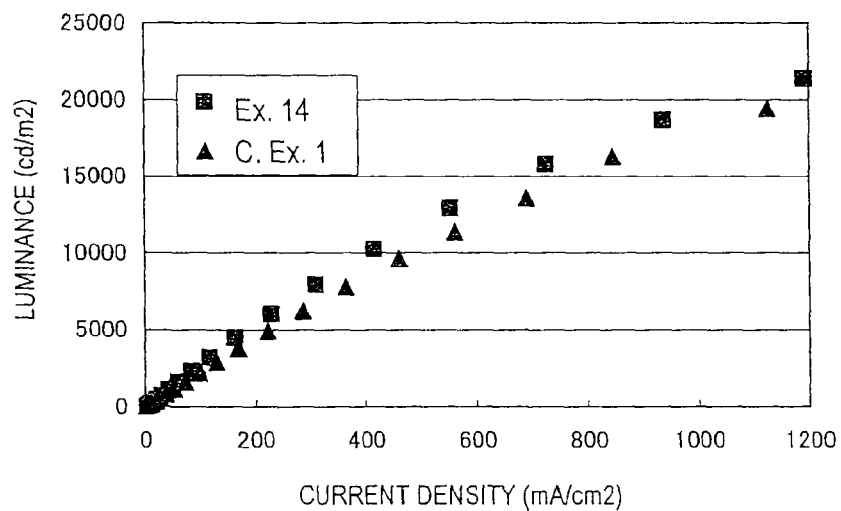
FIG. 17 is a graph comparing current density/luminance properties of Example 14 and Comparative Example 1.
Figure 18:
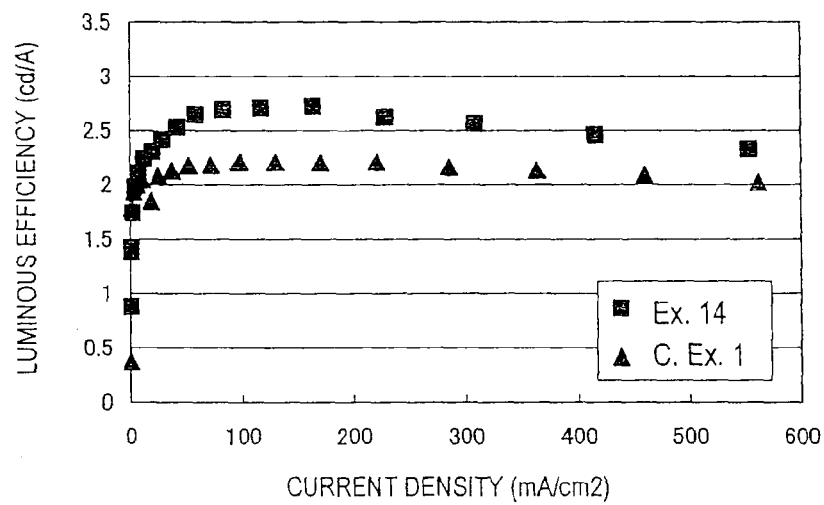
FIG. 18 is a graph comparing current density/luminous efficiency properties of Example 14 and Comparative Example 1.

An organic EL device was prepared by depositing a hole-injecting layer 3, a hole-transporting layer 4, an emitting layer 5, a hole-blocking layer 6, an electron-transporting layer 7, an electron-injecting layer 8, and a cathode (aluminum electrode) 9 in this order on a glass substrate 1 on which an ITO electrode had been formed in advance, as shown in FIG. 13. After the glass substrate 1 on which ITO having a film thickness of 150 nm had been formed was washed with an organic solvent, the surface was washed by UV ozone treatment. It was mounted into a vacuum deposition machine, which was then evacuated to 0.001 Pa.

Subsequently, CuPc was formed at a deposition rate of 3.6 nm/min to a thickness of about 20 nm as the hole-injecting layer 3 thereon. On the hole-injecting layer 3, NPD was formed at a deposition rate of 3.6 nm/min to a thickness of about 40 nm as the hole-transporting layer 4. On the hole-transporting layer 4, as the emitting layer 5, Alq was formed at a deposition rate of 3.6 nm/min to a thickness of about 30 nm. On the emitting layer 5, the compound of invention Example 4 (Compound 9) was formed at a deposition rate of 3.6 nm/min to a thickness of about 30 nm as the hole-blocking layer-cum-electron-transporting layer 6 and 7. On the hole-blocking layer-cum-electron-transporting layer 6 and 7, lithium fluoride was formed at a deposition rate of 0.36 nm/min to a thickness of about 0.5 nm as the electron-injecting layer 8. Finally, aluminum was deposited to a thickness of about 200 nm to form the cathode 9. The prepared device was stored in a vacuum desiccator and characteristic properties were measured in the atmosphere at ordinary temperature.

The results of measuring luminescence properties when direct voltage was applied to the organic EL device prepared using the compound of invention Example 4 (Compound 9) of the invention are summarized in Table 1.

Example 16

An organic EL device was prepared under the same conditions as in Example 15 except that the material of the hole-blocking layer-cum-electron-transporting layer 6 and 7 was replaced by the compound of invention Example 5 (Compound 10), and characteristic properties thereof were investigated.

The results of measuring luminescence properties when direct voltage was applied to the organic EL device prepared using the compound of invention Example 5 (Compound 10) of the invention are summarized in Table 1.

Example 17

An organic EL device was prepared under the same conditions as in Example 15 except that the material of the hole-blocking layer-cum-electron-transporting layer 6 and 7 was replaced by the compound of invention Example 6 (Compound 67), and characteristic properties thereof were investigated.

The results of measuring luminescence properties when direct voltage was applied to the organic EL device prepared using the compound of invention Example 6 (Compound 67) of the invention are summarized in Table 1.

Example 18

An organic EL device was prepared under the same conditions as in Example 15 except that the material of the hole-blocking layer-cum-electron-transporting layer 6 and 7 was replaced by the compound of invention Example 7 (Compound 124), and characteristic properties thereof were investigated.

The results of measuring luminescence properties when direct voltage was applied to the organic EL device prepared using the compound of invention Example 7 (Compound 124) of the invention are summarized in Table 1.

Example 19

An organic EL device was prepared under the same conditions as in Example 15 except that the material of the hole-blocking layer-cum-electron-transporting layer 6 and 7 was replaced by the compound of invention Example 8 (Compound 129), and characteristic properties thereof were investigated.

The results of measuring luminescence properties when direct voltage was applied to the organic EL device prepared using the compound of invention Example 8 (Compound 129) of the invention are summarized in Table 1.

Example 20

An organic EL device was prepared under the conditions the same as in Example 15 except that the material of the hole-blocking layer-cum-electron-transporting layer 6 and 7 was replaced by the compound of invention Example 9 (Compound 155), and characteristic properties thereof were investigated.

The results of measuring luminescence properties when direct voltage was applied to the organic EL device prepared using the compound of invention Example 9 (Compound 155) of the invention are summarized in Table 1.

Comparative Example 2

For comparison, an organic EL device was prepared under the same conditions as in Example 15 except that the material of the electron-transporting layer 7 was replaced by Alq3, and characteristic properties thereof were investigated.

TABLE 1

|  | Compound | Voltage [V] (@20 mA/cm$^2$) | Luminance [cd/m$^2$] (@20 mA/cm$^2$) | Luminous efficiency [cd/A] (@20 mA/cm$^2$) | Power efficiency [lm/W] (@20 mA/cm$^2$) |
| --- | --- | --- | --- | --- | --- |
| Example 15 | Compound 9 | 7.06 | 928 | 4.64 | 2.06 |
| Example 16 | Compound 10 | 6.68 | 1045 | 5.23 | 2.45 |
| Example 17 | Compound 67 | 5.96 | 943 | 4.72 | 2.48 |
| Example 18 | Compound 124 | 6.28 | 908 | 4.54 | 2.27 |
| Example 19 | Compound 129 | 6.71 | 930 | 4.65 | 2.17 |
| Example 20 | Compound 155 | 6.64 | 814 | 4.07 | 1.93 |
| Comparative Example 2 | Alq3 | 7.20 | 923 | 4.62 | 2.02 |

Thus, it was revealed that the organic El devices of the invention are excellent in luminous efficiency, can achieve remarkable decrease in driving voltage, and further are excellent in thermal resistance, as compared with the devices using Alq3 which is a commonly employed general electron-transporting material.

While the invention has been described in detail and with reference to specific embodiments thereof, it will be apparent to one skilled in the art that various changes and modifications can be made therein without departing from the spirit and scope thereof.

The present application is based on Japanese Patent Application No. 2006-222890 filed on Aug. 18, 2006, and the contents are incorporated herein by reference.

INDUSTRIAL APPLICABILITY

Since the compound having a pyridoindole ring structure having a substituted pyridyl group attached thereto according to the invention exhibits good injection of electrons and is stable in a thin-film state, the compound is excellent as a compound for organic EL devices. By preparing organic EL devices using the compound, driving voltage can be decreased and durability can be improved. For example, it becomes possible to spread the compound onto applications of electric home appliances and illumination.

The invention claimed is:

1. A compound having a pyridoindole ring structure having a substituted pyridyl group attached thereto, which is represented by the general formula (1):

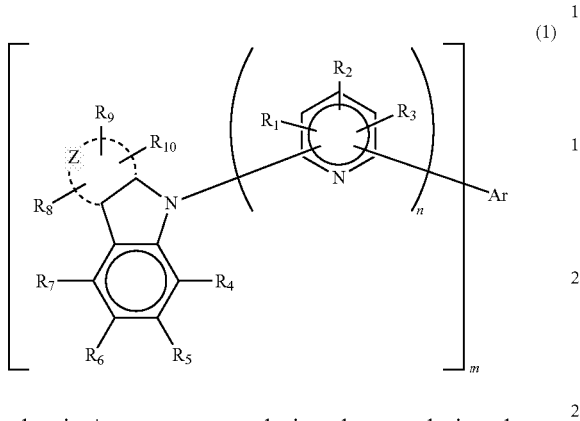

wherein Ar represents a substituted or unsubstituted aromatic hydrocarbon group, a substituted or unsubstituted aromatic heterocyclic group, or a substituted or unsubstituted condensed polycyclic aromatic group; R1 to R10 may be the same or different from one another and each independently represents a hydrogen atom, a fluorine atom, a cyano group, an alkyl group, or a substituted or unsubstituted aromatic hydrocarbon group; Z represents a 6-membered aromatic heterocyclic ring containing one nitrogen atom; and m and n each independently represents an integer of 1 wherein a substituent of said substituted aromatic heterocyclic group is selected from the group consisting of a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group a pyridoindolyl group, a quinolyl group, and a benzothiazolyl group;

and a substituent of said substituted aromatic hydrocarbon group is selected from the group consisting of a fluorine atom, a chlorine atom, a cyano group, a hydroxyl group, a nitro group, an alkyl group, a cycloalkyl group, an alkoxy group, an amino group, a naphthyl group, an anthryl group, a styryl group, a pyridyl group, a pyridoindolyl group, a quinolyl group, and a benzothiazolyl group, wherein Ar does not represent a pyrimidyl group.

2. An organic electroluminescent device comprising a pair of electrodes and at least one organic layer interposed between the electrodes, wherein at least one of the organic layer(s) contains the compound having a pyridoindole ring structure according to claim 1.

3. The organic electroluminescent device according to claim 2, wherein the organic layer(s) comprises an electron-transporting layer, and the compound represented by the general formula (1) is present in the electron-transporting layer.

4. The organic electroluminescent device according to claim 2, wherein the organic layer(s) comprises a hole-blocking layer, and the compound represented by the general formula (1) is present in the hole-blocking layer.

5. The organic electroluminescent device according to claim 2, wherein the organic layer(s) comprises an emitting layer, and the compound represented by the general formula (1) is present in the emitting layer.

6. The organic electroluminescent device according to claim 2, wherein the organic layer(s) comprises an electron-injecting layer, and the compound represented by the general formula (1) is present in the electron-injecting layer.

7. A compound having a pyridoindole ring structure having a substituted pyridyl group attached thereto, which is represented by the general formula (1):

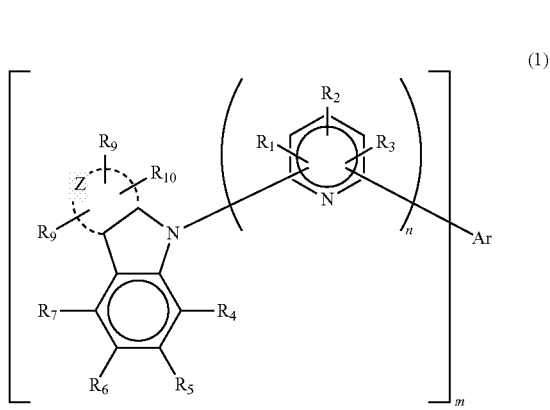

wherein Ar represents a substituted or unsubstituted aromatic heterocyclic group selected from the group consisting of a pyridyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, and an acridinyl group; R1 to R10 may be the same or different from one another and each independently represents a hydrogen atom, a fluorine atom, a cyano group, an alkyl group, or a substituted or unsubstituted aromatic hydrocarbon group; Z represents a 6-membered aromatic heterocyclic ring containing one nitrogen atom; and n is an integer of 1 and m is an integer of 2 or 3.

8. An organic electroluminescent device comprising a pair of electrodes and at least one organic layer interposed between the electrodes, wherein at least one of the organic layer(s) contains the compound having a pyridoindole ring structure according to claim 7.

9. The organic electroluminescent device according to claim 8, wherein the organic layer(s) comprises an electron-transporting layer, and the compound represented by the general formula (1) is present in the electron-transporting layer.

10. The organic electroluminescent device according to claim 8, wherein the organic layer(s) comprises a hole-blocking layer, and the compound represented by the general formula (1) is present in the hole-blocking layer.

11. The organic electroluminescent device according to claim 8, wherein the organic layer(s) comprises an emitting layer, and the compound represented by the general formula (1) is present in the emitting layer.

12. The organic electroluminescent device according to claim 8, wherein the organic layer(s) comprises an electron-injecting layer, and the compound represented by the general formula (1) is present in the electron-injecting layer.

* * * * *